(12) United States Patent
Melanson et al.

(10) Patent No.: US 11,634,280 B2
(45) Date of Patent: *Apr. 25, 2023

(54) AUTONOMOUS MOBILE DELIVERY ROBOT AND CHAIN OF CUSTODY SYSTEM

(71) Applicant: ST Engineering Aethon, Inc., Pittsburgh, PA (US)

(72) Inventors: Anthony Melanson, Wexford, PA (US); Ryan List, Beaver, PA (US); Spencer Allen, Wexford, PA (US); Scott E. Stropkay, Carlisle, MA (US); Andres Chamorro, III, Ashland, MA (US); Mark C. Matthews, Scituate, MA (US); Ashley James Nye Legg, Newton, MA (US)

(73) Assignee: ST Engineering Aethon Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/447,338

(22) Filed: Sep. 10, 2021

(65) Prior Publication Data

US 2022/0004979 A1 Jan. 6, 2022

Related U.S. Application Data

(63) Continuation of application No. 16/739,257, filed on Jan. 10, 2020, now Pat. No. 11,142,401.

(Continued)

(51) Int. Cl.
*G07C 9/00* (2020.01)
*B65G 1/137* (2006.01)
(Continued)

(52) U.S. Cl.
CPC ............ *B65G 1/1371* (2013.01); *B25J 5/007* (2013.01); *B25J 11/008* (2013.01); *B60P 3/00* (2013.01);
(Continued)

(58) Field of Classification Search
None
See application file for complete search history.

(56) References Cited

U.S. PATENT DOCUMENTS

| | | |
|---|---|---|
| 5,510,984 A | 4/1996 | Markin et al. |
| 5,905,653 A | 5/1999 | Higham et al. |
| | (Continued) | |

FOREIGN PATENT DOCUMENTS

WO 2018099930 A1 6/2018

OTHER PUBLICATIONS

International Search Report and Written Opinion of the International Searching Authority for PCT/US2020/013025, dated Mar. 16, 2020 (13 pages).

(Continued)

*Primary Examiner* — K. Wong
(74) *Attorney, Agent, or Firm* — Buchanan Ingersoll & Rooney PC

(57) ABSTRACT

Disclosed are a system and a method that includes a robotic unit configured to deliver items (e.g., medicine, foodstuff, linens, equipment, etc.) to sites (e.g., rooms, offices, etc.) and/or individuals (e.g., patients, pharmacists, technician, etc.) throughout a facility (e.g., hospital, office building, mailroom, manufacturing facility, etc.). The robotic unit is a mobile unit that operates autonomously to follow predetermined or programmed routes throughout the facility to deliver the items. The system is configured to maintain a chain of custody for the items. In addition, the robotic unit is configured to only allow designated items to be delivered to designated sites and/or to authorized individuals. This can be achieved by the robotic unit having a plurality of containers that are locked within a storage space of the robotic unit, and are only accessible upon successful completion of an authorization process.

20 Claims, 24 Drawing Sheets

Related U.S. Application Data

(60) Provisional application No. 62/791,331, filed on Jan. 11, 2019.

(51) Int. Cl.

| | | |
|---|---|---|
| *G06Q 50/28* | (2012.01) | |
| *G07C 9/20* | (2020.01) | |
| *B25J 5/00* | (2006.01) | |
| *B25J 11/00* | (2006.01) | |
| *B60P 3/00* | (2006.01) | |
| *G05D 1/00* | (2006.01) | |
| *G06F 21/33* | (2013.01) | |
| *G06Q 10/0832* | (2023.01) | |
| *G06Q 10/1093* | (2023.01) | |

(52) U.S. Cl.
CPC ........... *G05D 1/0088* (2013.01); *G06F 21/33* (2013.01); *G06Q 10/0832* (2013.01); *G06Q 50/28* (2013.01); *G07C 9/00896* (2013.01); *G07C 9/215* (2020.01); *G05D 2201/0206* (2013.01); *G05D 2201/0211* (2013.01); *G06Q 10/1097* (2013.01); *G07C 2009/0092* (2013.01); *G07C 2209/63* (2013.01)

(56) References Cited

U.S. PATENT DOCUMENTS

| | | |
|---|---|---|
| 8,068,023 B2 * | 11/2011 | Dulin .................... G01S 5/0205 |
| | | 340/572.1 |
| 9,489,490 B1 | 11/2016 | Theobald |
| 9,535,421 B1 | 1/2017 | Canoso et al. |
| 9,741,010 B1 | 8/2017 | Heinla |
| 9,911,341 B2 | 3/2018 | Soundararajan et al. |
| 9,919,420 B1 | 3/2018 | Theobald |
| 10,328,769 B2 | 6/2019 | Ferguson et al. |
| 11,142,401 B2 * | 10/2021 | Melanson .............. G16H 40/20 |
| 2003/0020383 A1 | 1/2003 | Yuyama et al. |
| 2004/0113786 A1 | 6/2004 | Maloney |
| 2006/0125356 A1 | 6/2006 | Meek, Jr. et al. |
| 2011/0137457 A1 | 6/2011 | Zini et al. |
| 2018/0024554 A1 | 1/2018 | Brady et al. |
| 2020/0223632 A1 | 7/2020 | Melanson et al. |

OTHER PUBLICATIONS

Extended European Search Report for European Application No. 20739061-8 dated Nov. 9, 2022.

\* cited by examiner

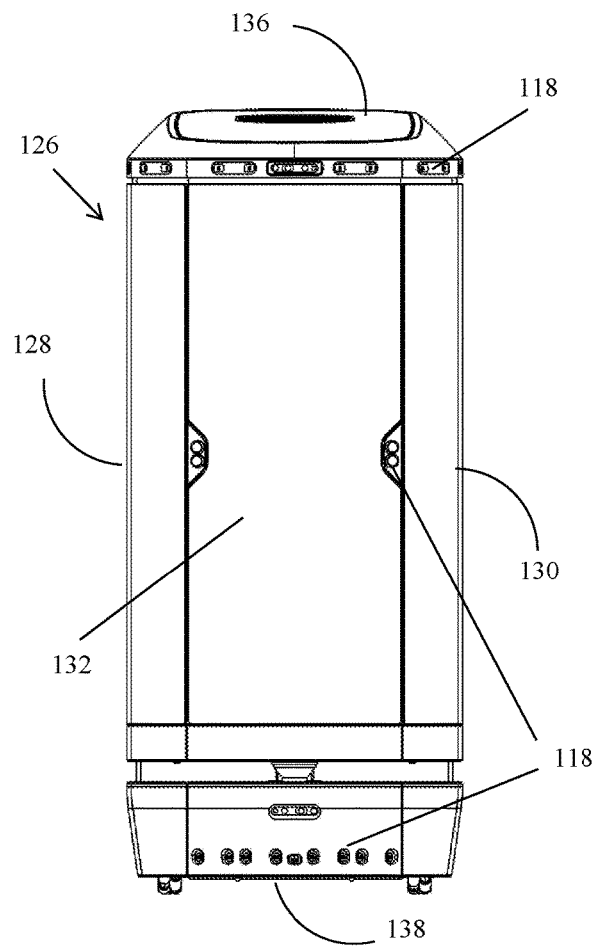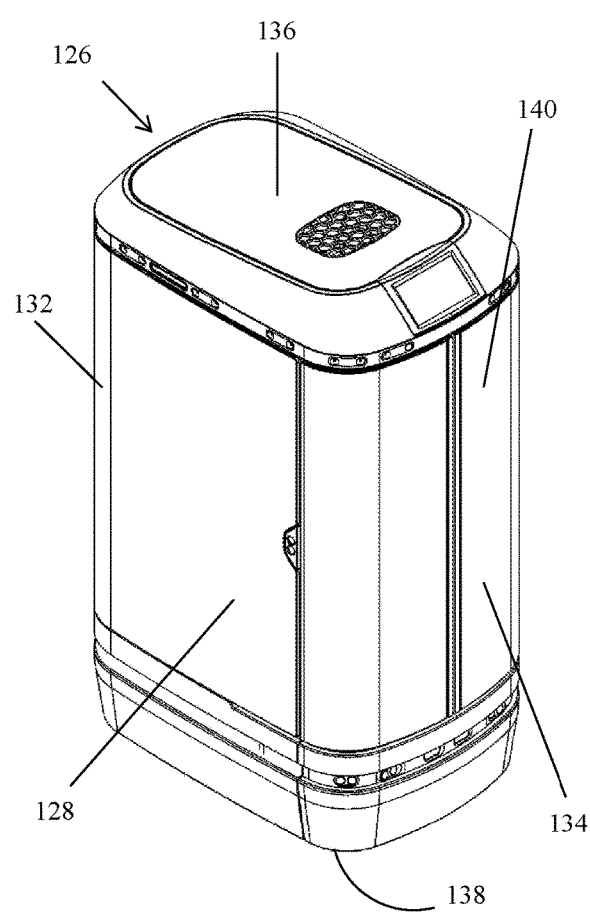
FIG. 5A                    FIG. 5B

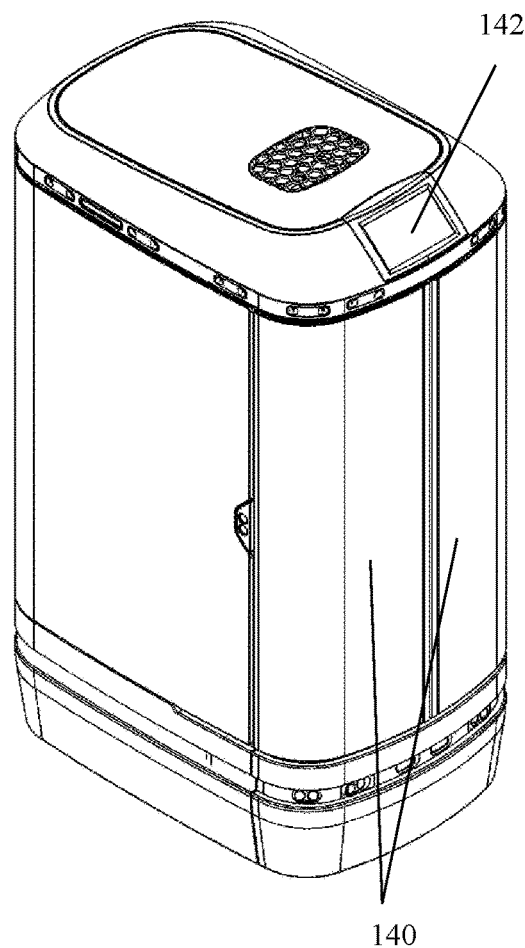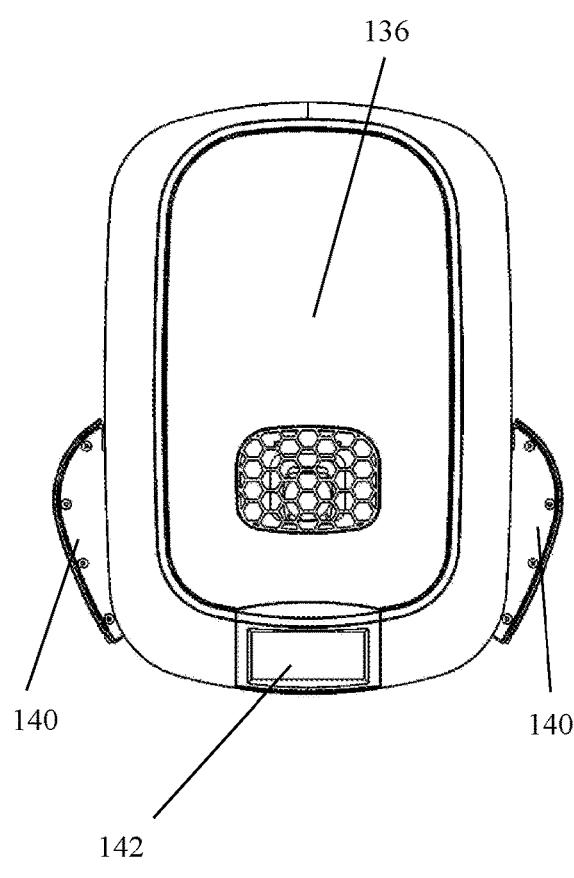
FIG. 7A
FIG. 7B

AUTONOMOUS MOBILE DELIVERY ROBOT AND CHAIN OF CUSTODY SYSTEM

CROSS-REFERENCE TO RELATED APPLICATIONS

This patent application is a continuation application of co-pending U.S. patent application Ser. No. 16/739,257, filed on Jan. 10, 2020, which claims the benefit of U.S. Provisional Patent Application No. 62/791,331, filed on Jan. 11, 2019, the entire disclosures of which are hereby incorporated by reference herein in their entireties.

FIELD OF THE INVENTION

Embodiments relate to systems and methods for delivering items via an autonomous robotic unit whose payload is configurable to meet differing delivery objectives including those which require the chain of custody for the items.

BACKGROUND OF THE INVENTION

Conventional systems for delivering items using robotic means are limited in that they rely on static configurations of the delivery payload as well as fail to provide a means to facilitate selective distribution of the items and a chain of custody for the items.

The present invention is designed to overcome at least one of the above identified problems.

BRIEF SUMMARY OF THE INVENTION

Embodiments of the system include a robotic unit configured to deliver items (e.g., goods, packages, supplies, medicine, foodstuff, linens, equipment, etc.) to sites (e.g., rooms, offices, stations, etc.) and/or individuals (e.g., guests, residents, staff, patients, pharmacists, technician, etc.) throughout a facility (e.g., hotel, convention center, residential tower, hospital, office building, mailroom, manufacturing facility, etc.). The robotic unit is a mobile unit that operates autonomously and along generally defined or pre-defined routes throughout the facility to deliver the items. The robotic unit operating along generally defined or pre-defined routes involves the robotic unit following a route but can deviate from the route to avoid collisions, follow a detour, pursue a more or less optimal path, etc. The robotic unit has a storage space with a plurality of containers that are removably secured therein. The containers can have various shapes, configurations, and features to provide a flexible, modular delivery system. Any one or combination of types of containers can be used for a desired delivery schedule. This can be done to provide a robotic delivery system that is flexibly reconfigured to meet a desired purpose. For instance, embodiments of the robotic unit can be used in a hotel setting to deliver items such as towels to patrons and/or staff at a room location or other area, and be reconfigured to deliver snacks and drinks to residents of the hotel, and be reconfigured to securely deliver food (e.g., room service) to hotel guest's rooms, etc. It should be noted that the robotic unit can be used or reconfigured for use in other settings, such as hospital settings (e.g., to deliver pharmaceuticals, medical supplies, etc.), office settings (e.g., to deliver mail, office supplies, etc.), residential settings (e.g., to deliver parcels and packages), manufacturing environments, etc.

The flexibility of the re-configurability of the robotic unit resides in the modular nature of the containers (may be referred to herein as inserts) used in the robotic unit. The containers can be of any type or size and can be interchangeable. For instance, the containers can be bins, trays, sub-cabinets, etc. Any of the containers can configured as drink holders, snack holders, towel holders, parcel and package holders, food tray holders, medication holders etc. The containers can be lockable so as to facilitate delivery of secured items. Thus, the robotic unit can be configured to deliver secured items in lockable containers and non-secured items in non-lockable containers. Locking containers can be different forms including cabinets, drawers, bins or lockers. The various types of containers, the lockable and non-lockable nature of the containers, and the interchangeability of the containers within the robotic unit provides for a modular/flexible design for multi-purpose use.

Any of the items can be provided with tracking markers to facilitate generating chain of custody information. For example, any one or combination of the items can be associated with a barcode, RFID tag, infrared-detectable marker, etc. Sensors or scanners on the robotic unit can track the presence, absence, or location of an item that has been marked with a marker to generate information that will be part of the chain of custody information. The chain of custody information can include when and where the container was accessed, when and where the item was removed from the container, who accessed the container and/or item, if an item had been delivered or not, if an item had been delivered to a specified individual and/or location, etc. In some embodiments, the chain of custody feature can be selectively activated or deactivated. The activation or deactivation can be initiated by manual selection by a user or automatically via satisfaction of some other condition. For example, the chain of custody feature can be activated when an item is placed within a lockable container. As will be explained in detail later, the lockable container can only be unlocked via entering an access code. The access code can be associated with a specific individual and paired to the delivery location. Thus, an individual accessing the container via the access code when the robot arrives at a specified destination can be used to compile the chain of custody information.

It is contemplated for the robotic unit to be an autonomous unit that follows generally defined or pre-defined routes as it makes deliveries. This can involve following predetermined paths throughout a facility, navigating autonomously to programmed destinations, using external inputs (e.g., wireless devices, sensors, cameras etc.) to assist with navigation, etc.

As a non-limiting example, the system can be configured for use in a hospitality setting (e.g., a hotel). The robotic unit can have a plurality of first type containers carrying various beverage items (e.g., the first type containers can have drink holders). The robotic unit can have a plurality of second type containers carrying various snack food items (e.g., the second type containers can have snack holders). The robotic unit can have a plurality of third type containers carrying various hotel room and bathroom products, such as cosmetics, toiletries, towels, etc. As the robotic unit roams about the hotel or follows a predetermined path, items can be accessed or delivered to hotel guests and staff. Any of the first, second, or third type containers can be removed and replaced by another type of container to allow the robotic unit to accommodate a specific demand for an item, to follow a specific delivery schedule, etc.

For instance, the robotic unit can be configured for use as a vending unit. In this case, the robotic unit could have a plurality of first type containers carrying drinks and second type containers carrying snacks. The robotic unit is locked so as to only be accessed by a user (e.g., a hotel guest) who enters a recognized access code. For example, hotel guest can be given an access code or token when registering with the hotel. This access code can allow them open the door (e.g., unlock the door) of the robotic unit and/or gain access to the containers within the robotic unit. In this situation, the chain of custody tracking feature can be initiated as soon as the robotic unit has been unlocked via input of an access code. The chain of custody information can track whether an item has been removed from the robotic unit via, for example, RFID tags placed on the items. The chain of custody information can track which hotel guest removed which item, and charge them appropriately.

In addition, the robotic unit is configured to only allow designated items to be delivered to designated sites and/or to authorized individuals. This can be achieved by the robotic unit having a plurality of containers that are locked within a storage space of the robotic unit, and are only accessible upon successful completion of an authorization process. The authorization process can be entry of a code into a user interface of the robotic unit, proof of identity provided by the individual, entrance of the robotic unit into a known location on the map of the site, etc. For instance, sticking with the hospitality setting example, the robotic unit can be made to travel throughout a hotel with a plurality of lockable containers, each container configured to carry a tray of food (e.g., food ordered via room service). The robotic unit travels to room-1 designated as a location for delivery of food order-1. The hotel guest of room-1 can enter his/her access code and be allowed to access container-1 to retrieve food order-1, but cannot access any other container within the robotic unit. The robotic unit travels to room-2 designated as a location for delivery of food order-2. The hotel guest of room-2 can enter his/her access code and be allowed to access container-2 to retrieve food-order-2, but cannot access any other container within the robotic unit.

As another non-limiting example, the robotic unit can be made to travel throughout a residential setting (e.g., an apartment complex, a condominium complex, etc.) with a plurality of lockable containers, each container configured to carry a parcel or package. The robotic unit travels to apartment-1 designated as a location for delivery of parcel-1. The apartment resident of apartment-1 can enter his/her access code and be allowed to access container-1 to retrieve parcel-1, but cannot access any other container within the robotic unit. The robotic unit travels to apartment-2 designated as a location for delivery of parcel-2. The apartment resident of apartment-2 can enter his/her access code and be allowed to access container-2 to retrieve parcel-2, but cannot access any other container within the robotic unit.

In some embodiments, the robotic unit will not grant access to the item unless the robotic unit is at the designated location and the correct access code is received. In other words, the user has to be at the delivery location and enter the correct access code in order to gain access to the container. For instance, the apartment resident of apartment-1 must be located at the appointed delivery location for apartment-1 and enter his/her access code to be allowed to access container-1 to retrieve parcel-1.

A benefit of the disclosed system is the ability to provide a flexible, modular delivery system by which a robotic unit follows delivery routes and delivers different types of items based on the type of container(s) used. In addition, using the delivery schemes disclosed herein are beneficial in that the robotic unit can make multiple types of deliveries (e.g., delivery of restricted items and non-restricted items) by following a single delivery schedule or delivery route, but by only allowing authorized individuals to access the restricted items. Conventional systems and methods, however, require use of delivery units and delivery routes to transport restricted items that are separate and distinct from delivery units and delivery routes to transport non-restricted items.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages and possible applications of the present invention will be more apparent from the following more particular description thereof, presented in conjunction with the following drawings, in which:

FIG. 5A shows a front view of an exemplary embodiment of the robotic unit, and FIG. 5B shows a rear perspective view of an exemplary embodiment of the robotic unit.

FIG. 7A shows a rear perspective view of an exemplary embodiment of the robotic unit with its doors in a closed position, and FIG. 7B shows a top view of an exemplary embodiment of the robotic unit with its doors in an open position.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
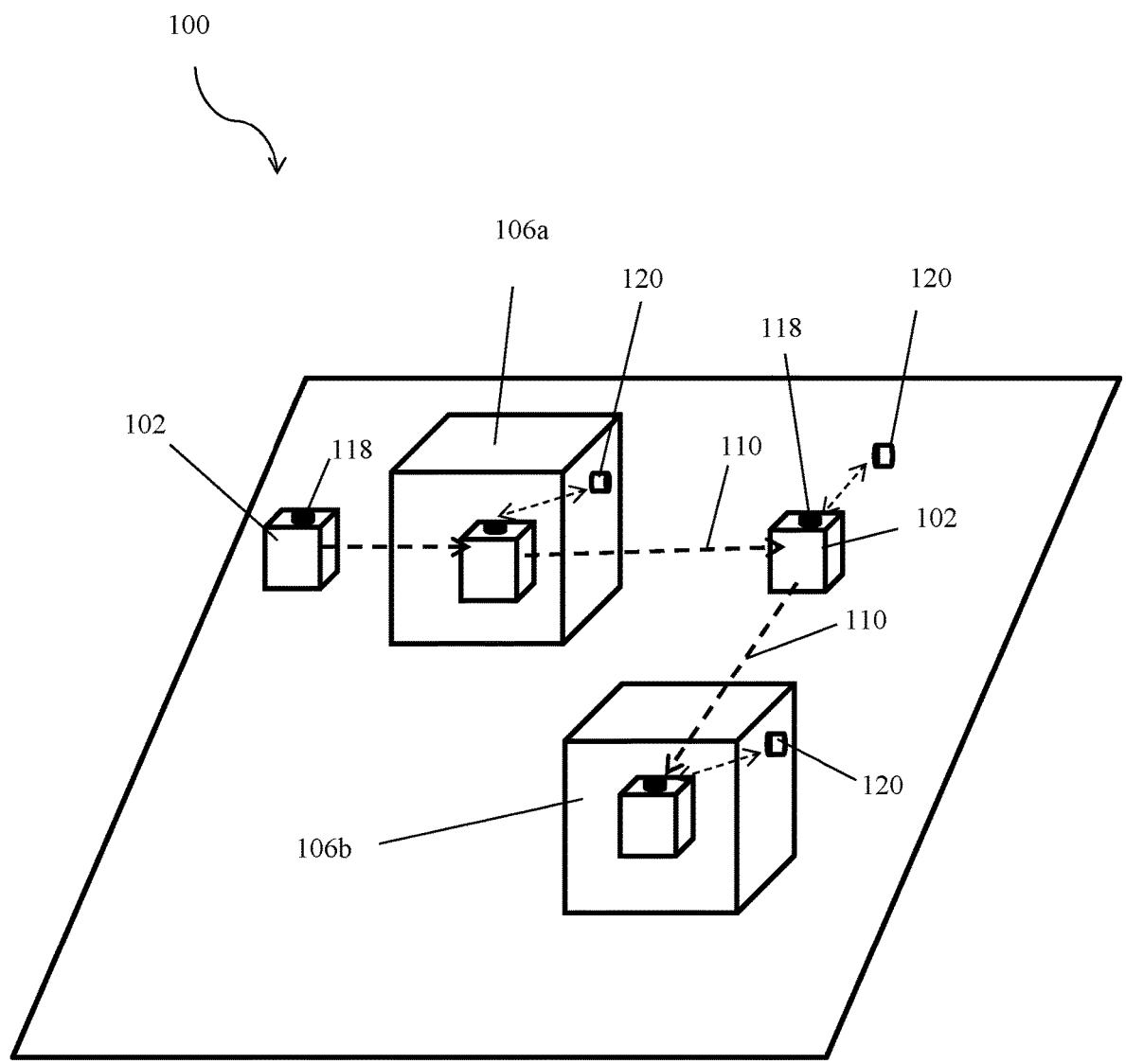
FIG. 1 shows an exemplary block diagram of any embodiment of the system, illustrating an embodiment of a robotic unit following a delivery route.
Figure 2:
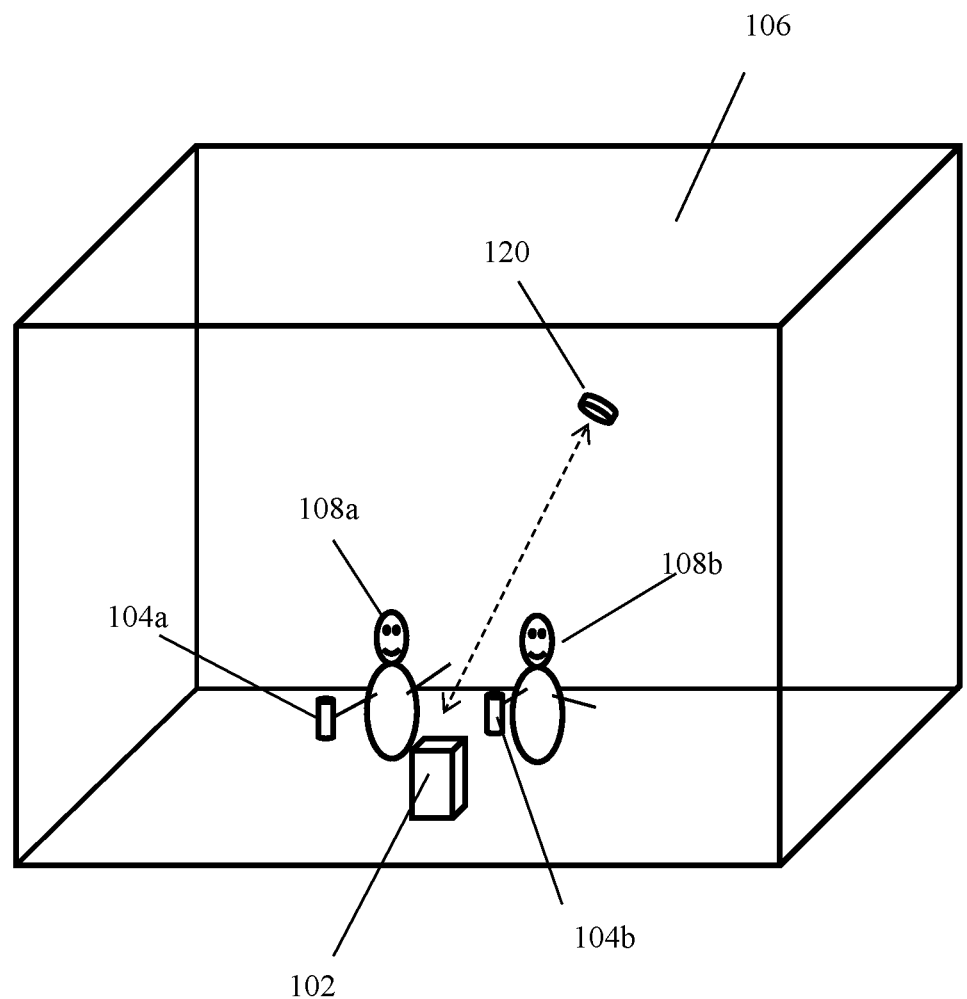
FIG. 2 shows an embodiment of the robotic unit selectively delivering items to individuals.
Figure 3:
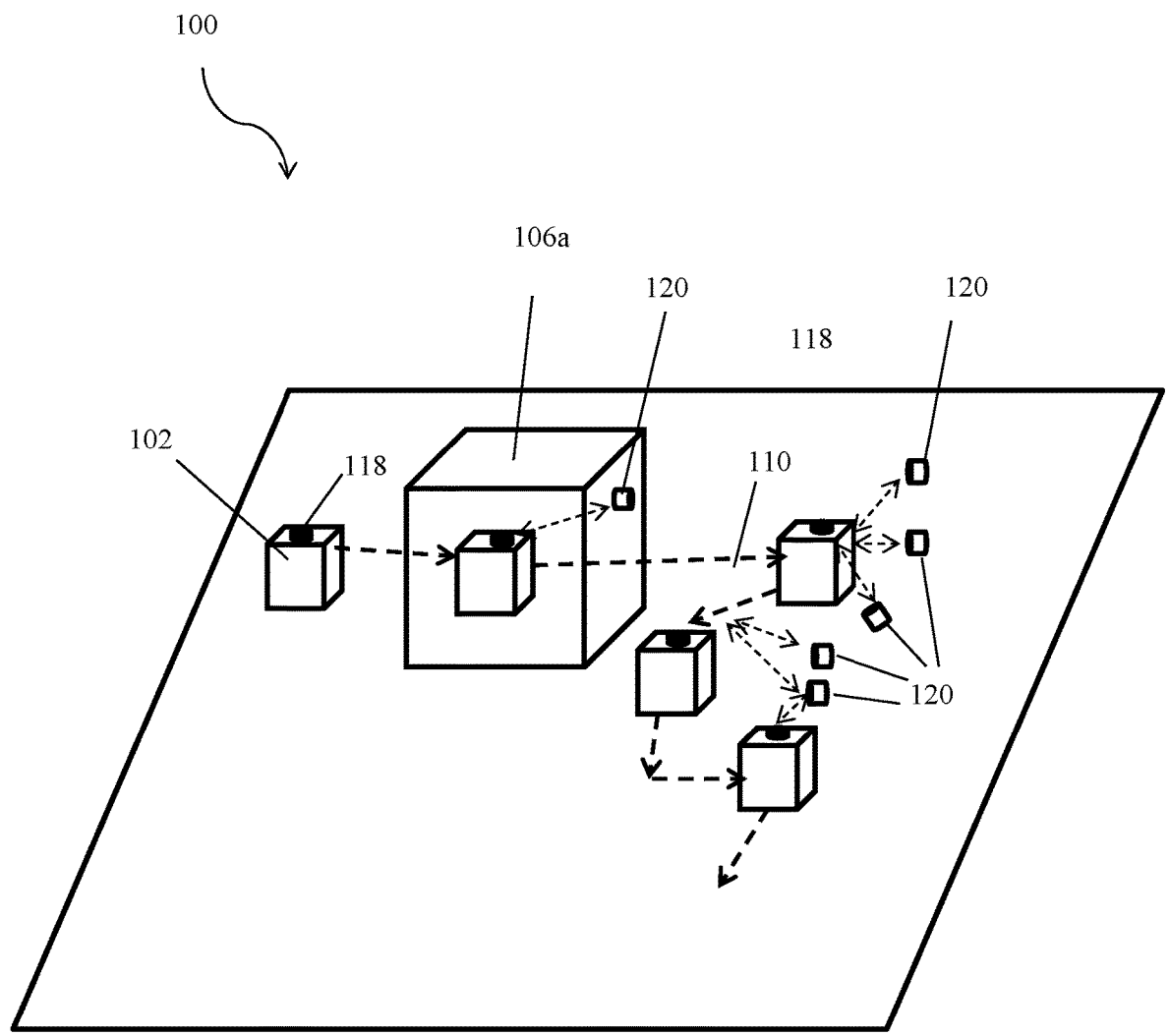
FIG. 3 shows an exemplary block diagram of any embodiment of the system, illustrating an embodiment of a robotic unit following a delivery route and being caused to make a detour.

Referring to FIGS. 1-3, embodiments of the system 100 include at least one robotic unit 102 configured to deliver items 104 to sites 106 and/or individuals 108. The robotic unit 102 is a mobile unit that operates autonomously to follow predetermined or programmed routes or paths 110 throughout a facility (e.g., hotel) to deliver items 104 (e.g., beverages, snacks, towels, etc.) to sites 106 (e.g., rooms) and/or individuals 108 (e.g., guests, staff, etc.). The system 100 is configured to maintain a chain of custody for the items 104. In addition, the robotic unit 102 is configured to only allow designated items 104 to be delivered to designated sites 106 and/or authorized individuals 108. For example, item-A 104a may be designated for delivery to individual-A 108a, and thus the robotic unit 102 can transport item-A 104a to a site 106 where many individuals 108 are located but only allow individual-A 108a to access item-A 104a from a storage space 112 within the robotic unit 102. This can be achieved by the robotic unit 102 having a plurality of containers 114 that are locked within the storage space 112 of the robotic unit 102 and are only accessible upon successful completion of an authorization process. The containers 114 are preferably modular containers of different sizes to allow a range of elements to be transported by the robotic unit 102. The authorization process can be entry of a code into a user interface 116 (see FIG. 22) of the robotic unit 102, proof of identity provided by the individual 108, entrance of the robotic unit 102 into known location on the map of the site 106, etc.

It is contemplated for embodiments of the system 100 to be used in a hospitality setting, but it will be understood that the system 100 can be used in other settings, such as an office building, a mailroom, a manufacturing facility, hospital, apartment complex, condominium complex, etc.

The robotic unit 102 has a motor in electro-mechanical connection with wheels, the motor being configured to receive signals from a processor of the robotic unit 102 that causes the robotic unit 102 to travel. For example, the processor causes the motor to drive the wheels or so as to cause the robotic unit 102 to move in a desired direction. Any of the processors disclosed herein can be an integrated circuit, a central processing unit, a microprocessor, a core processor, a mother board, a computer device, etc. in operative association with a non-volatile, non-transitory memory. The memory can be a data store, a database, a memory of a server (this can include a cloud-based server), etc. Any of the processors can include a means to transmit signals to and from other components of the system 100. These signals can be command signals, data acquisition signals from sensors, data input signals entered by users, etc. The transmission means can be achieved via a hardwire transmission or wireless transmission (e.g., use of transceivers, gateways, etc.).

The processor of the robotic unit 102 is configured to execute instructions stored on the memory that cause the robotic unit 102 to make deliveries. This can include causing the robotic unit 102 to travel from site 106 and/or individual 108 to site 106 and/or individual 108 in accordance with a generally determined or pre-determined path 110 and/or delivery schedule. For example, the processor can be programmed to cause the robotic unit 102 to travel to site-A 106a at a predetermined time to deliver item-A 104a, and then to site-B 106b at a predetermined time to deliver item-B 104b, etc. As another example, the processor can be programmed to cause the robotic unit 102 to travel to site-A 106a to deliver item-A 104a, and then wait for further instructions, whereupon receiving the further instructions it travels to site-B 106b to deliver item-B 104b. As another example, the processor can be programmed to cause the robotic unit 102 to travel along a predetermined path 110 and/or follow a delivery schedule unless it receives instructions to deviate from the predetermined path 110 and/or the delivery schedule. This deviation can be permanent (e.g., establishing a new predetermined path 110 and/or the delivery schedule) or temporary (e.g., establishing and following a detour). It will be appreciated by one skilled in the art that other delivery schemes can be derived and programmed into the processor of the robotic unit 102.

The robotic unit 102 includes at least one robotic unit sensor 118 (e.g., proximity sensor, motion sensor, RADAR unit, LIDAR unit, sound sensor, light sensor, optical camera, infrared camera, RFID scanner, biometric scanner, etc.). The robotic unit sensor(s) 118 is configured to facilitate navigation of the robotic unit 102, allowing the robotic unit 102 to travel along desired paths 110 and without running into objects or persons. The robotic unit sensor 118 can also allow the robotic unit 102 to navigate about the facility to the various sites 106 and individuals 108 that are part of the delivery schedule by collecting data to allow the processor of the robotic unit 102 to calculate and follow the most efficient route 110, calculate and following detours, avoid impact with objects, persons, or other robotic units 102, etc.

It is contemplated for the robotic unit 102 to be an autonomous unit that delivers the items 104 from site 106 and/or individual 108 to site 106 and/or individual 108 automatically. As a non-limiting example, the processor of the robotic unit 102 is programmed to follow a generally determined or predetermined path 110, as defined by a floor plan of the facility. This can include following a map of the facility that has been saved on the memory associated with the processor of the robotic unit 102. The processor of the robotic unit 102 causes the robotic unit 102 to follow the predetermined path 110 while simultaneously avoiding objects in its path 110, making detours when necessary, accessing elevators to change floors, etc. This can be achieved by the robotic unit sensor 118 obtaining a scan (e.g., a LIDAR scape, RADAR scape, images, a soundscape, etc.) that is a representation of the surrounding environment within which the robotic unit 102 is operating. Object recognition, signal processing (e.g., Fourier transforms, Gabor filtering, etc.), and other object identification and navigation techniques can be used to process the scan and identify obstacles in the predetermined path 110, as well as the movement of the obstacles relative to the robotic unit 102. The processor of the robotic unit 102 can also be in communication with processors of elevator controllers, for example, to allow the robotic unit 102 to access and utilize the elevator for transport.

As noted herein, the robotic unit 102 can use a map of a floor plan of the facility and its own internal awareness to allow the robotic unit 102 to navigate throughout the facility and to determine its position therein at any given time. For instance, once the robotic unit 102 arrives at site 106, the robotic unit 102 can cross-reference its location with coordinates on the map to determine that it is in fact at site 106. Site-A 106 can be room # xyz in a hotel, for example. Thus, in accordance with the floor plan and the known position of the robotic unit 102 on that floor plan, the system can validate that the site 106 is room #xyz, its desired location.

Optionally, or possibly in addition to the map, external sensors and/or cameras 120 can be used to assist the robotic unit 102 in navigation and localization. For example, cameras/sensors 120 can be located throughout the facility. As the robotic unit 102 travels, the cameras/sensors 120 communicate with the robotic unit 102 or computer system 124 to follow a certain path 110, validate that the path 110 being taken is the correct path 110, prevent the robotic unit 102 from entering an unauthorized or non-optimal area, identify an area as a site 106 to which the robotic unit 102 is programmed to make a delivery, etc. For instance, the processor of the robotic unit 102 can be programmed to cause the robotic unit 102 to travel along path-A 110 to site-A 106a, the path 110 being defined by the floor plan recorded into the memory associated with the processor of the robotic unit 102. There may be several paths 110 to take, but the robotic unit 102 collects camera/sensor 120 information as it travels to ensure that it is taking path-A 110, or that path-A 110 is the most efficient or safe route to take. Upon reaching its destination, as defined by the floor plan, the robotic unit 102 acquisitions data from a camera/sensors 120 located at the site 106 to identify the destination as site-A 106a. If the information obtained from the camera 120 is determined as being a camera/sensors 120 associate with site-A 106a, then the system 100 validates that the robotic unit 102 has reached a destination that is in fact at site-A 106a.

The robotic unit 102 can then make its way to site-B 106b in accordance with the delivery schedule, following path-B 110 for example. On the way to site-B 106b, the robotic unit 102 may receive a robotic unit sensor signal indicating that a portion of path-B 110 has been isolated or blocked off. This robotic unit sensor signal may be from camera/sensors 120 that emits a signal indicating that an area in which any possible path 110 that runs through the area is off-limits (see FIG. 3). Isolating or blocking off an area within the facility can be achieved via dynamic navigation and real-time mapping techniques. The robotic unit 102 can use navigation techniques to generate a detour for delivery to site-B 106b, the detour being a calculated route 110 around the cordoned area.

In addition, or in the alternative, the system 100 can generate a cordoned off area to which the robotic unit 102 is confined. This can be done to marshal the robotic unit 102 to a specific area in the facility, cause the robotic unit 102 to only travel possible paths 110 within the cordoned area, and/or derive the detour path 110 for the robotic unit 102 by limiting the possible paths 110 that can be taken to the cordoned area.

Figure 4:
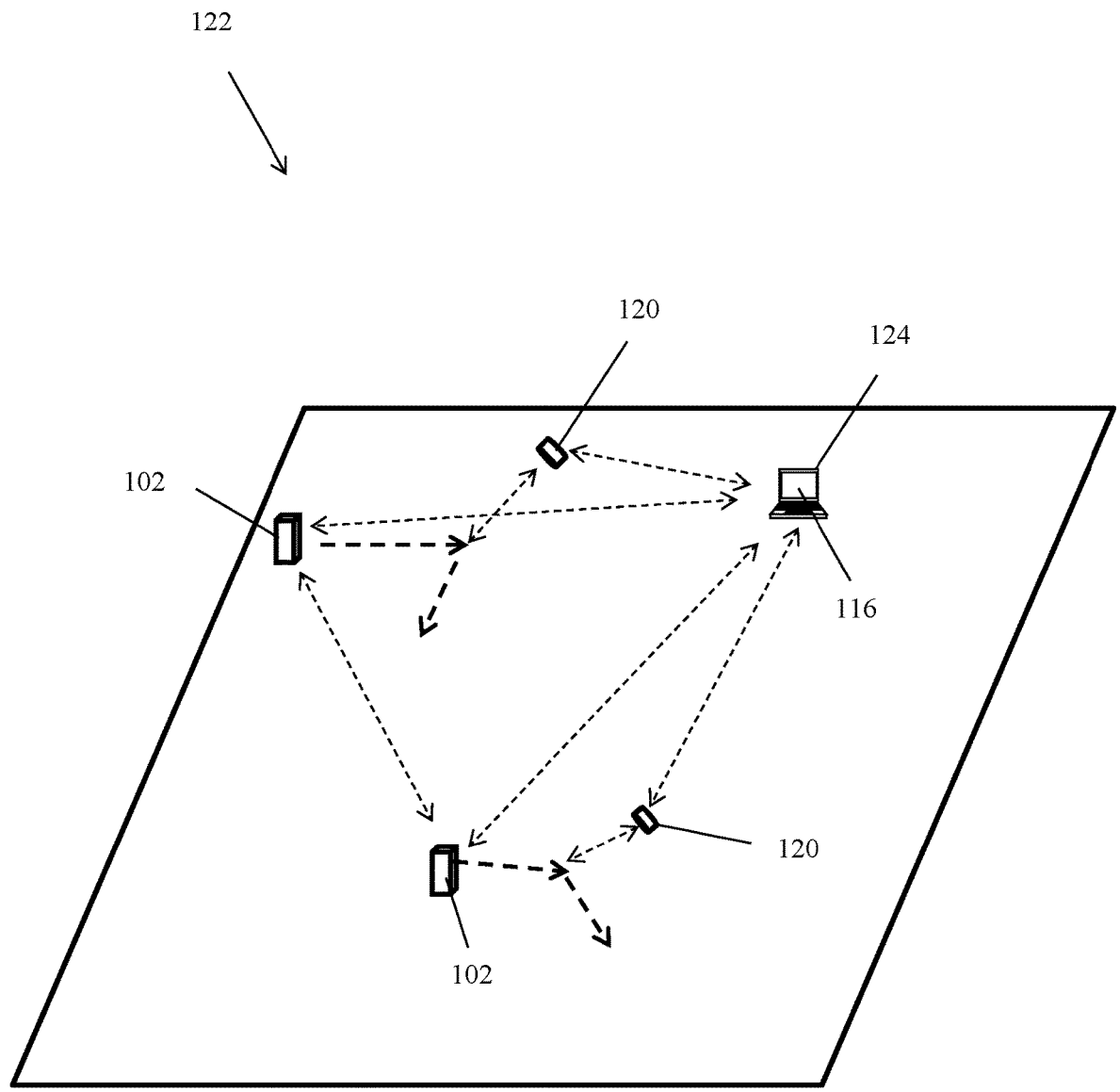
FIG. 4 shows an embodiment of the system communicating with a computer device via an exemplary communications network.
Figure 6:
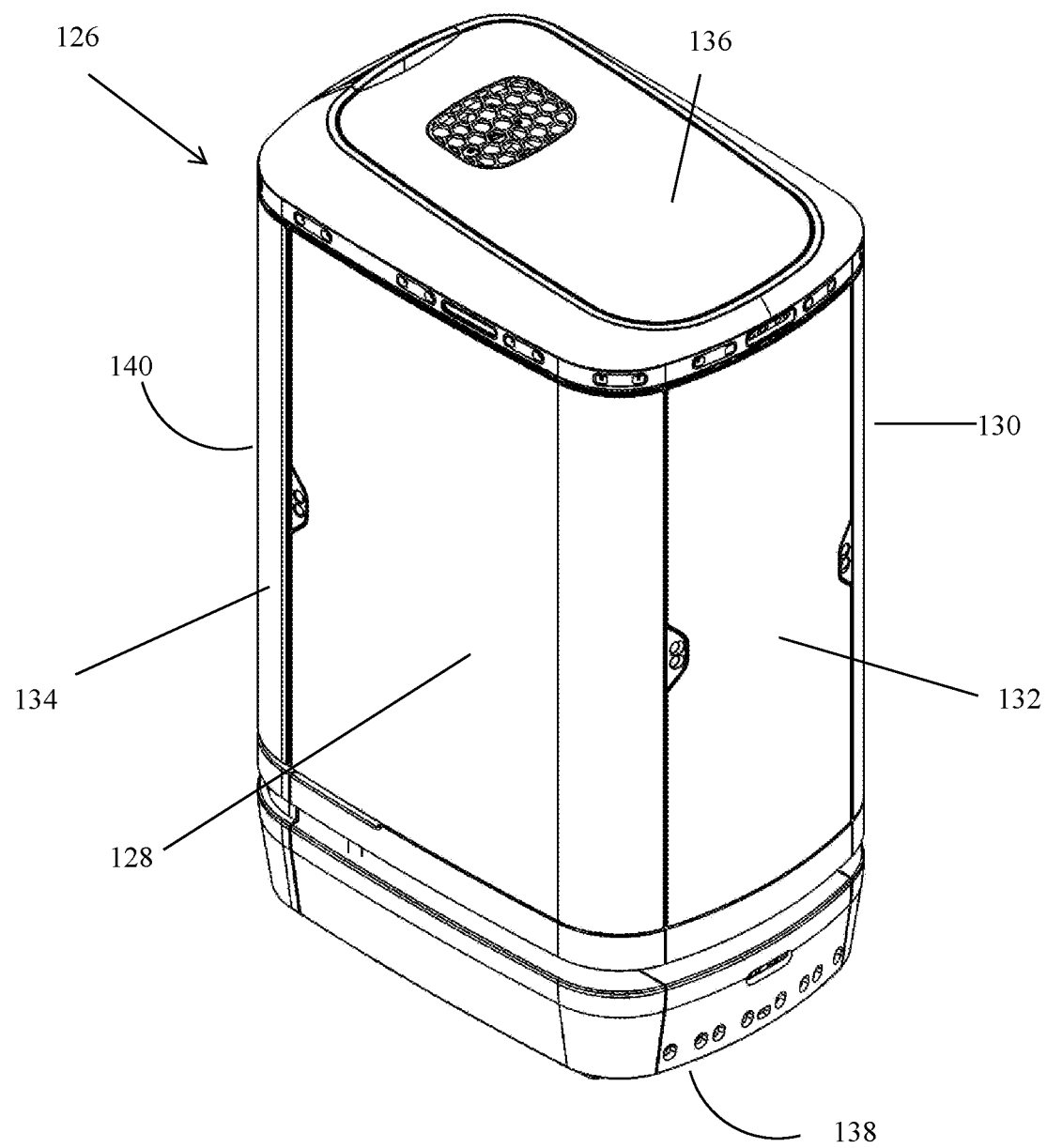
FIG. 6 shows a front perspective view of an exemplary embodiment of the robotic unit.

Referring to FIG. 4, as will be explained later, an embodiment of the system 100 can be configured to be part of a communications network 122 in which the robotic unit 102 is in communication with at least one computer device 124 of the communications network 122. It is contemplated for the computer device 124 to be part of a computer system operated by the facility or remotely at a data center. The computer device 124 can be used to communicate with the robotic unit 102 and/or the cameras/sensors 120. In addition, or in the alternative, the computer device 124 can communicate directly with the robotic unit 102 based on the information from the cameras/sensors 120 to cause the robotic unit 102 to take certain paths 110, make certain detours, etc.

As explained herein, the robotic unit 102 can be used to deliver items 104 to designated sites 106 and/or authorized individuals 108. A designated site 106 can be one in which the robotic unit 102 identifies as a site 106 matching the item 104 to be delivered to in accordance with the delivery schedule. This can be achieved by the robotic unit 102 arriving at a site 106 in accordance with the floor plan, the robotic unit 102 receiving other information (e.g., validating information form a user, validating information from a computer device 124 in communication with the robotic unit 102, etc.), etc.

In addition, the robotic unit 102 can be configured to not grant access to its storage space 112 (the portion of the robotic unit 102 containing the items 104) unless the robotic unit 102 has arrived at its designated site 106. Again, this can include arriving at a site 106 in which the robotic unit 102 identifies as a site 106 matching the item 104 to be delivered to in accordance with the delivery schedule, arriving at a site 106 in accordance with the floor plan, the robotic unit 102 receiving other information (e.g., validating information from a user, validating information from a computer device 124 in communication with the robotic unit 102, etc.), etc. In some embodiments, the robotic unit 102 is configured to not grant access to its storage space 112 unless the robotic unit 102 is proximate (e.g., within a predetermined distance) a camera/sensor 120 that is within or otherwise associated with the designated site 106. This can be achieved via mapping techniques, signal analysis, sensor fusion techniques, etc.

Granting access to authorized individuals 108 will be explained later, but it should be noted that the robotic unit 102 can be further configured to not grant access to its storage space 112 and/or a specific container 114 unless the individual 108 receiving the items 104 is identified as an authorized person in accordance with the delivery schedule. In some embodiments, the robotic unit 102 is configured to not allow access to the storage space 112 and/or a specific container 114 unless the individual 108 is identified as being authorized in addition to the robotic unit 102 being within a designated site 106.

Figure 8A:
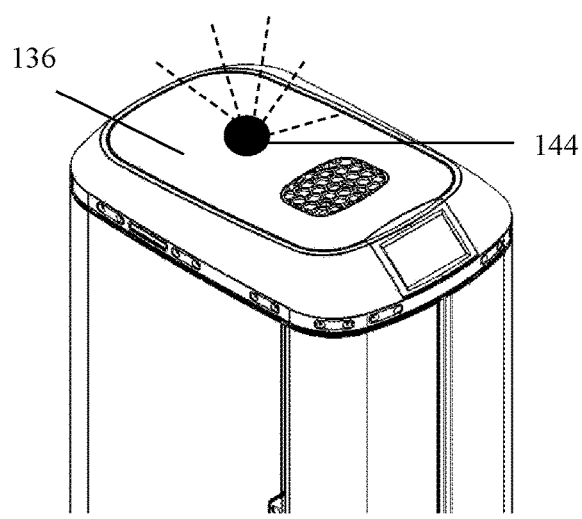
FIG. 8A shows an exemplary emergency stop button positioned on a top portion of an embodiment of the robotic unit with the emergency stop button being activated.
Figure 8B:
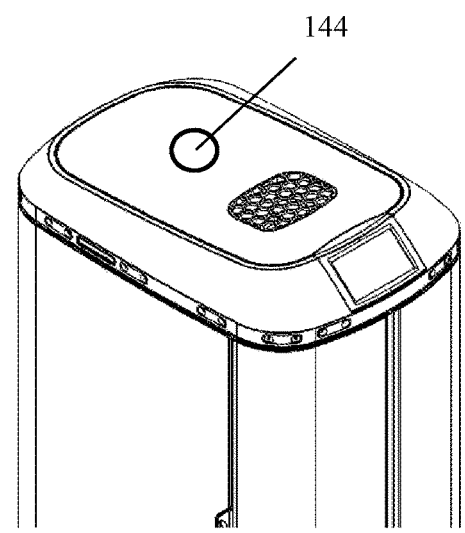
FIG. 8B shows an exemplary emergency stop button positioned on a top portion of an embodiment of the robotic unit with the emergency stop button being de-activated.
Figure 9:
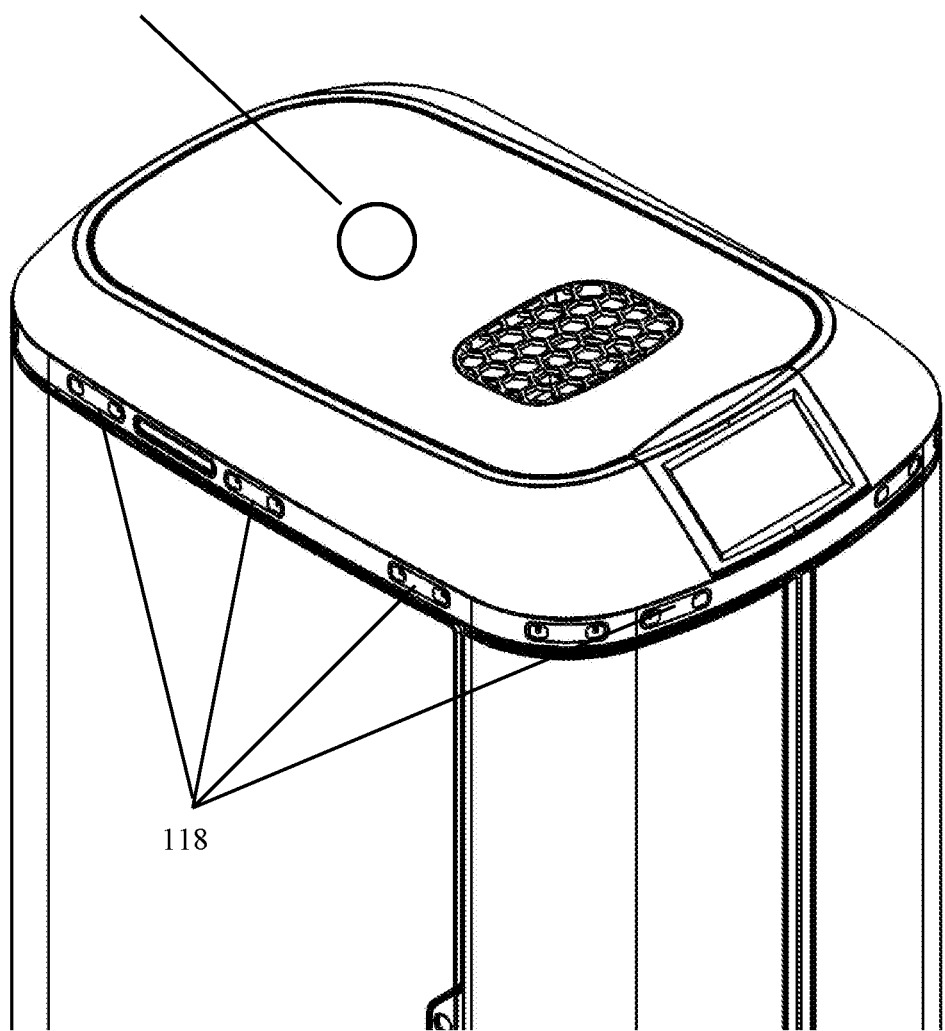
FIG. 9 shows exemplary robotic unit sensor placement for an embodiment of the robotic unit.

Referring to FIGS. 5-10, the robotic unit 102 has a housing 126 with a housing first side 128, housing second side 130, housing front 132, housing rear 134, housing top 136, and a housing bottom 138. The robotic unit sensors 118 can be placed anywhere on the housing 126. As a non-limiting example, FIG. 9 shows the robotic unit sensors 118 being located around a circumferential edge of a portion of the housing 128 at or near the housing top 136. Placing the robotic unit sensors 118 around the circumferential edge can allow the robotic unit 102 to generate a 360° scan of the surrounding environment. It should be noted that the robotic unit sensors 118 can be placed at other locations (e.g., the housing front 132 at or near the middle portion of the housing 126, around a circumferential edge of a portion of the housing 128 at or near the housing bottom 138, etc.).

Referring to FIGS. 8A-8B, some embodiments of the robotic unit 102 can include an emergency stop button 144.

The emergency stop button 144 can be depressed to cause the robotic unit 102 to stop moving, to lock its wheels or tracks, to shut down, etc. In some embodiments, the robotic unit 102 can be configured to transmit an alert signal (e.g., transmit an alert signal to a computer device 124), sound an audible alarm, emit a visible signal (see FIG. 8A), etc. when the emergency stop 144 button has been activated. It is contemplated for the emergency stop button 144 to be located on the housing top 136 for easy access and visibility for a user, but the emergency stop button 144 can be located anywhere on the housing 126.

Figure 10:
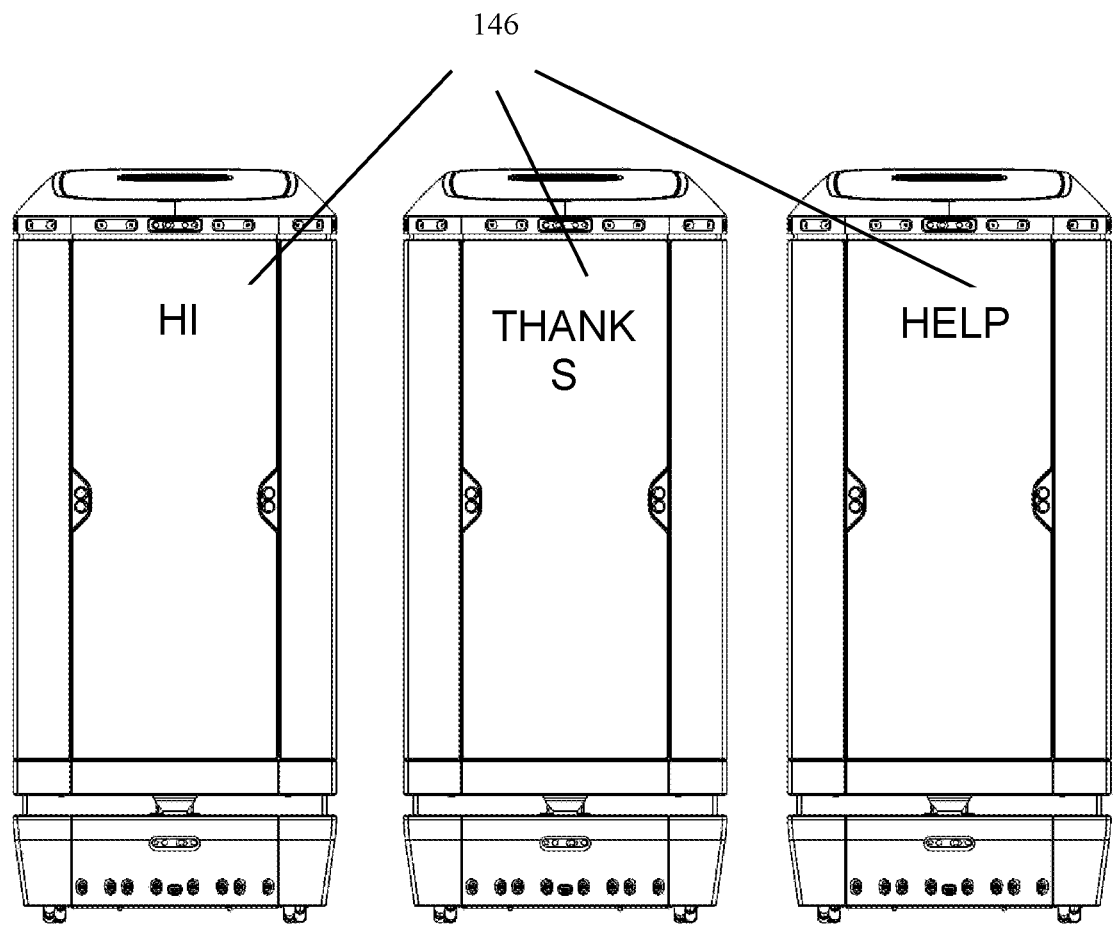
FIG. 10 shows an exemplary message panel for an embodiment of the robotic unit.

Referring to FIG. 10, in some embodiments, the housing 126 includes a message panel 146. The message panel 146 can be a LED array, LCD array, etc. configured to display textual and/or graphical massages. The textual and/or graphical massages can be a greeting, an informational message (e.g., informing a user where the robotic unit 102 is headed, if there is a malfunction, etc.), an advertisement, a logo, etc.

Figure 11:
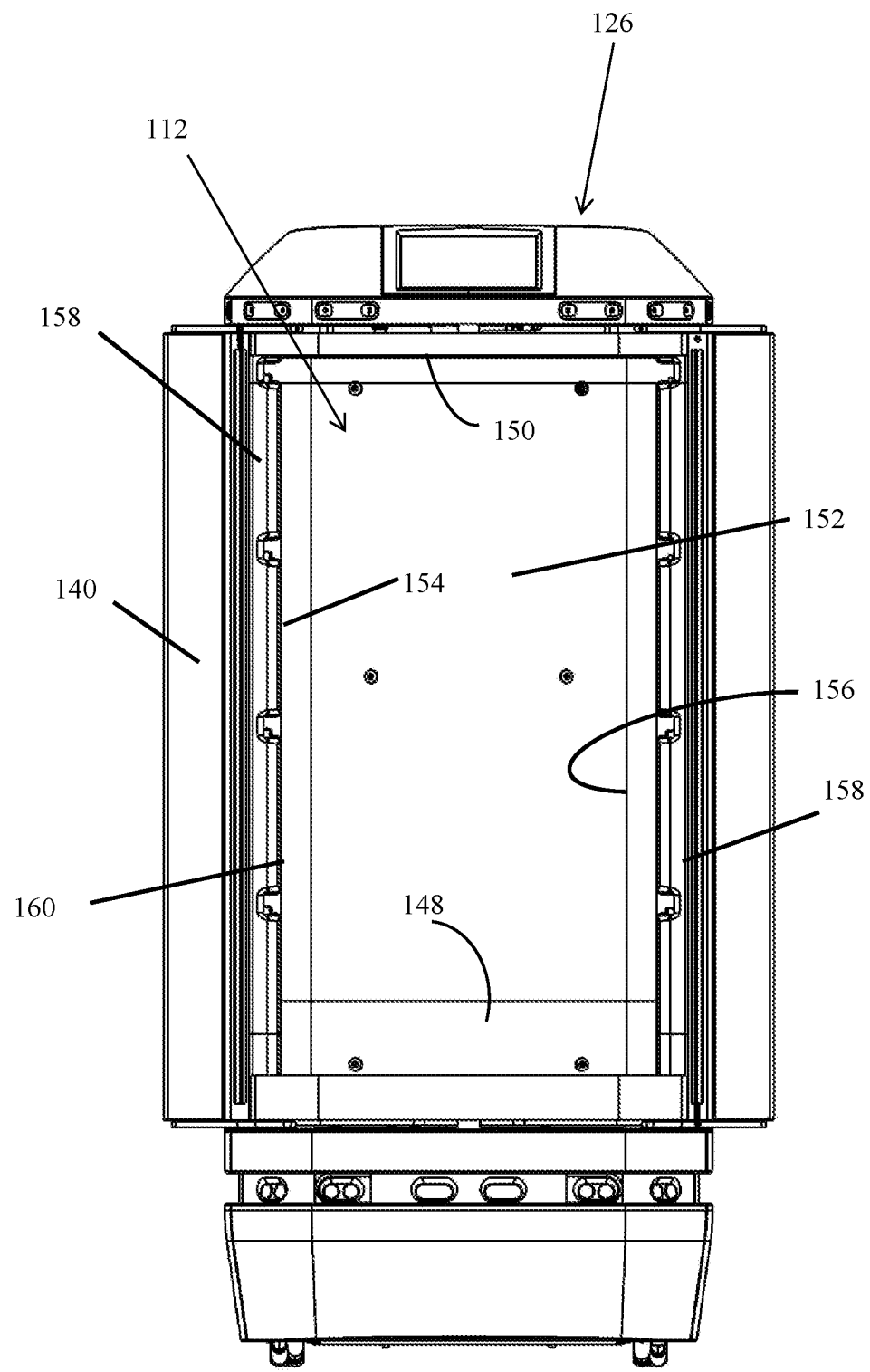
FIGS. 11-13 show exemplary storage space configurations that can be used for embodiments of the robotic unit.
Figure 12:
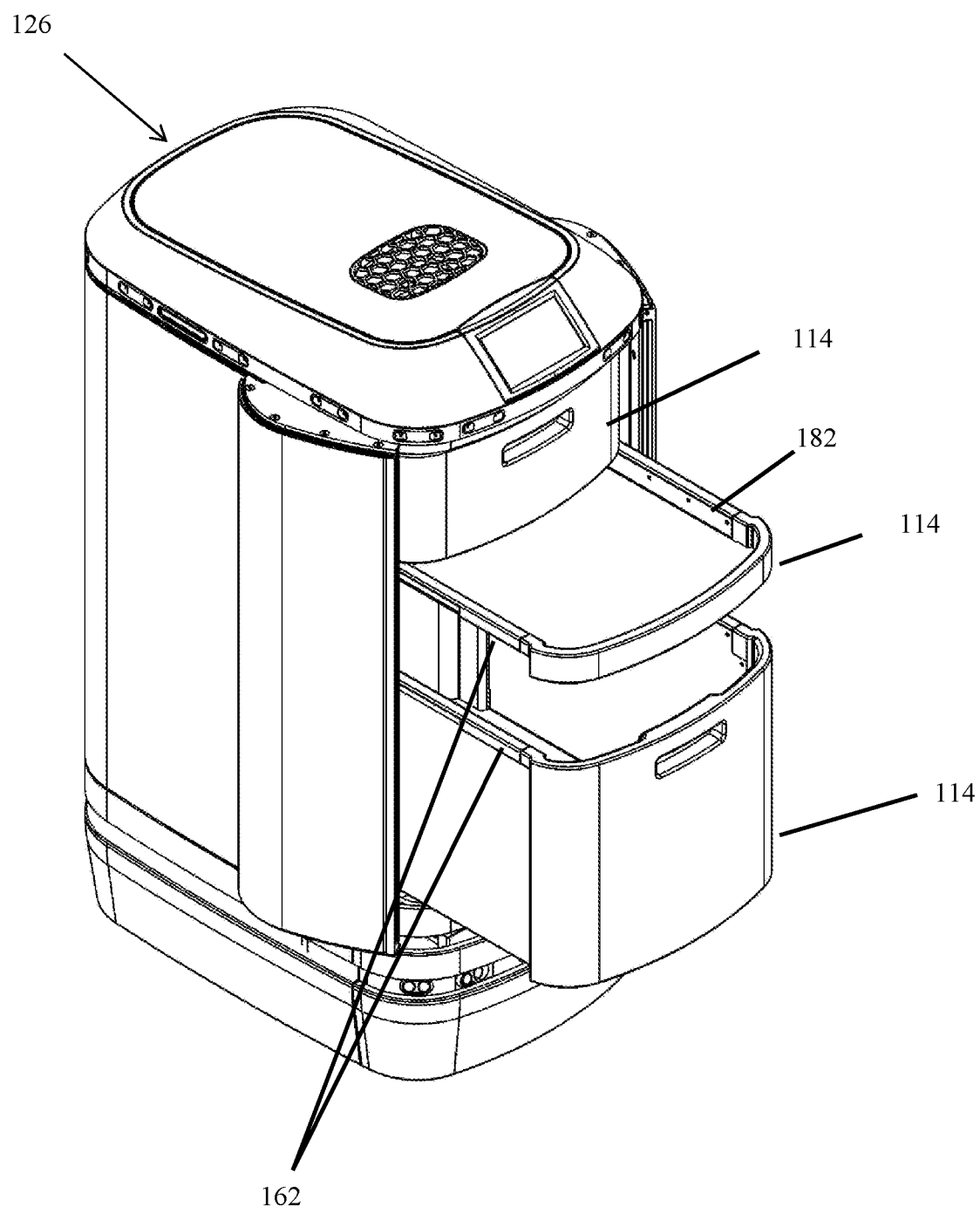
Figure 13:
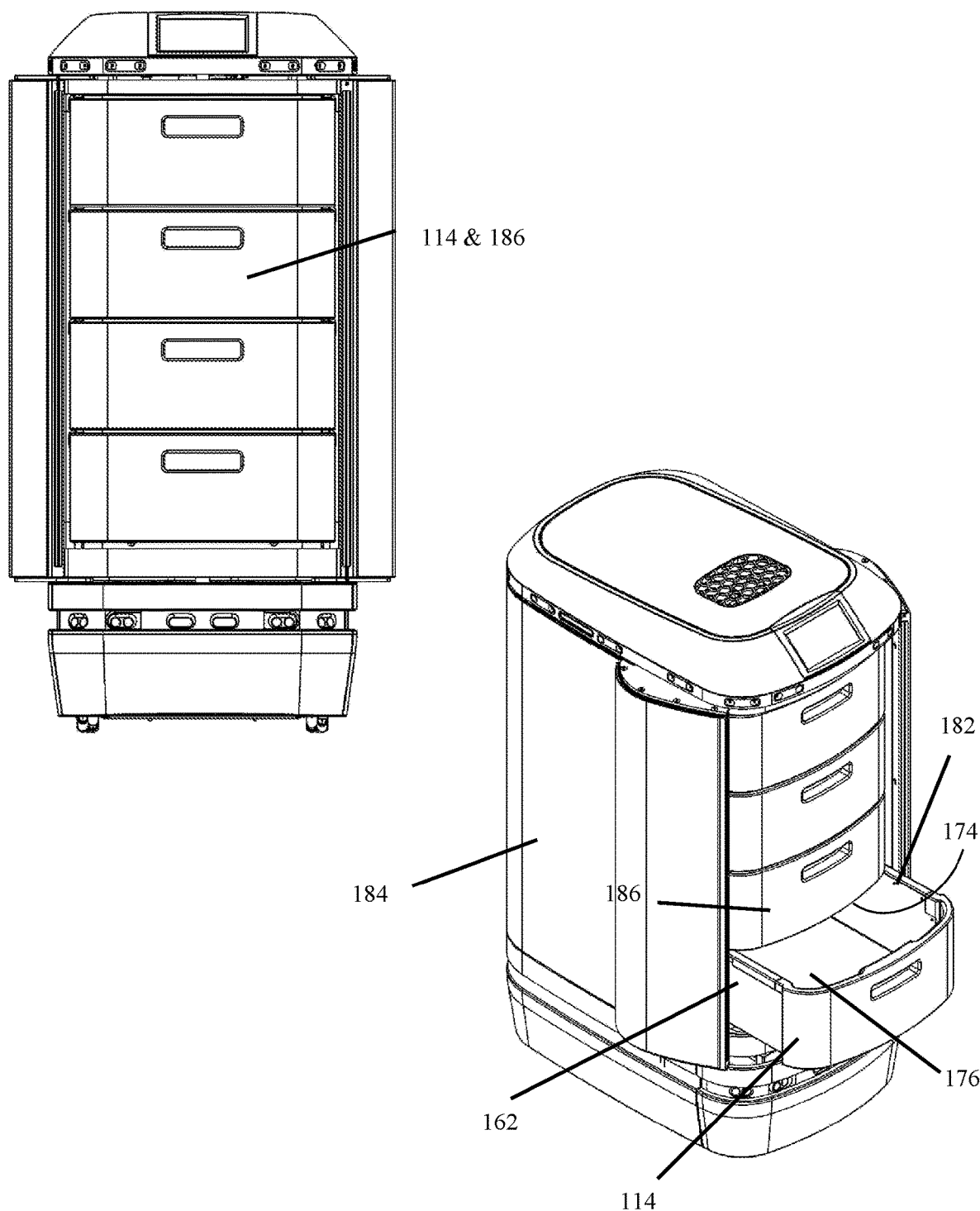
Figure 14:
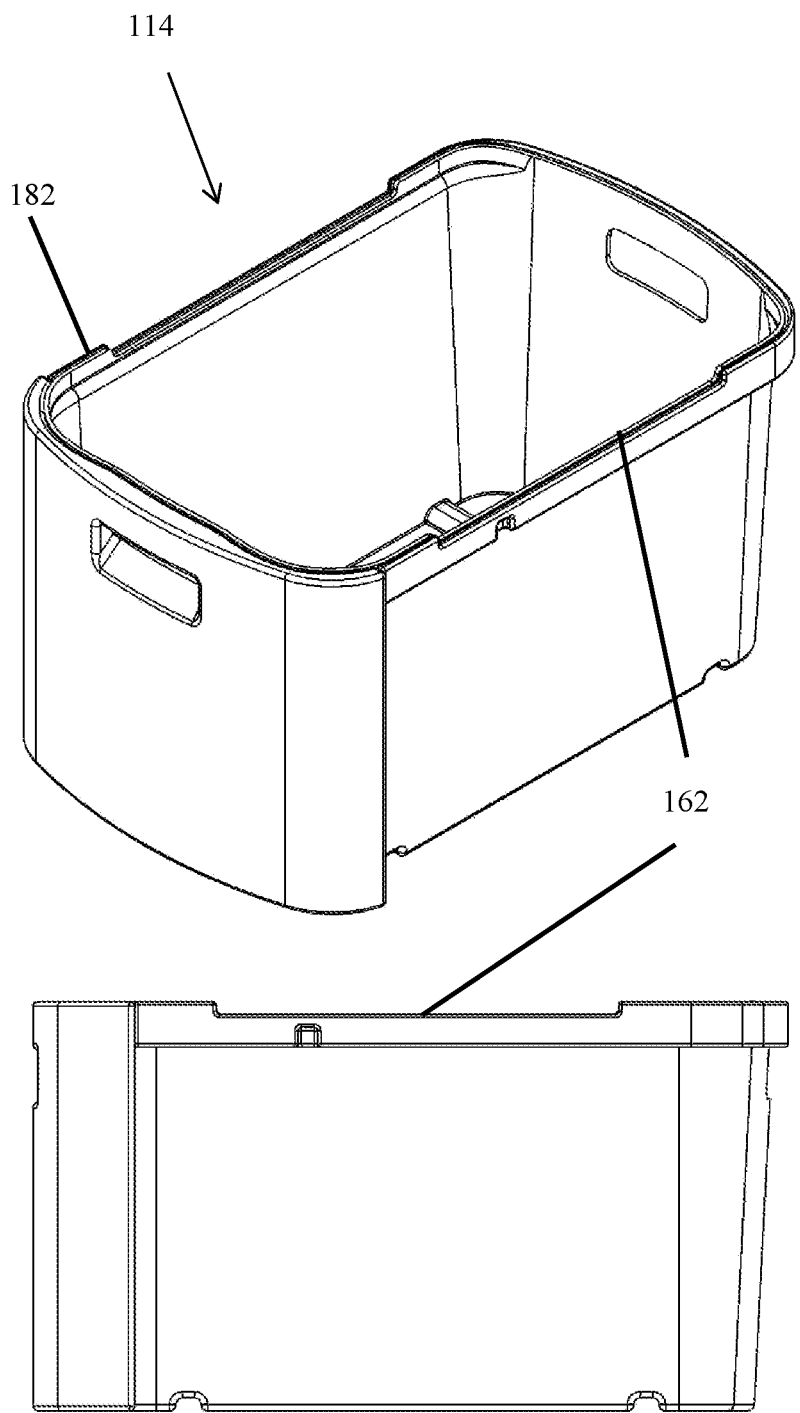
FIG. 14 shows a perspective and side view of exemplary container with its rail that can be used for an embodiment of the container.
Figure 15:
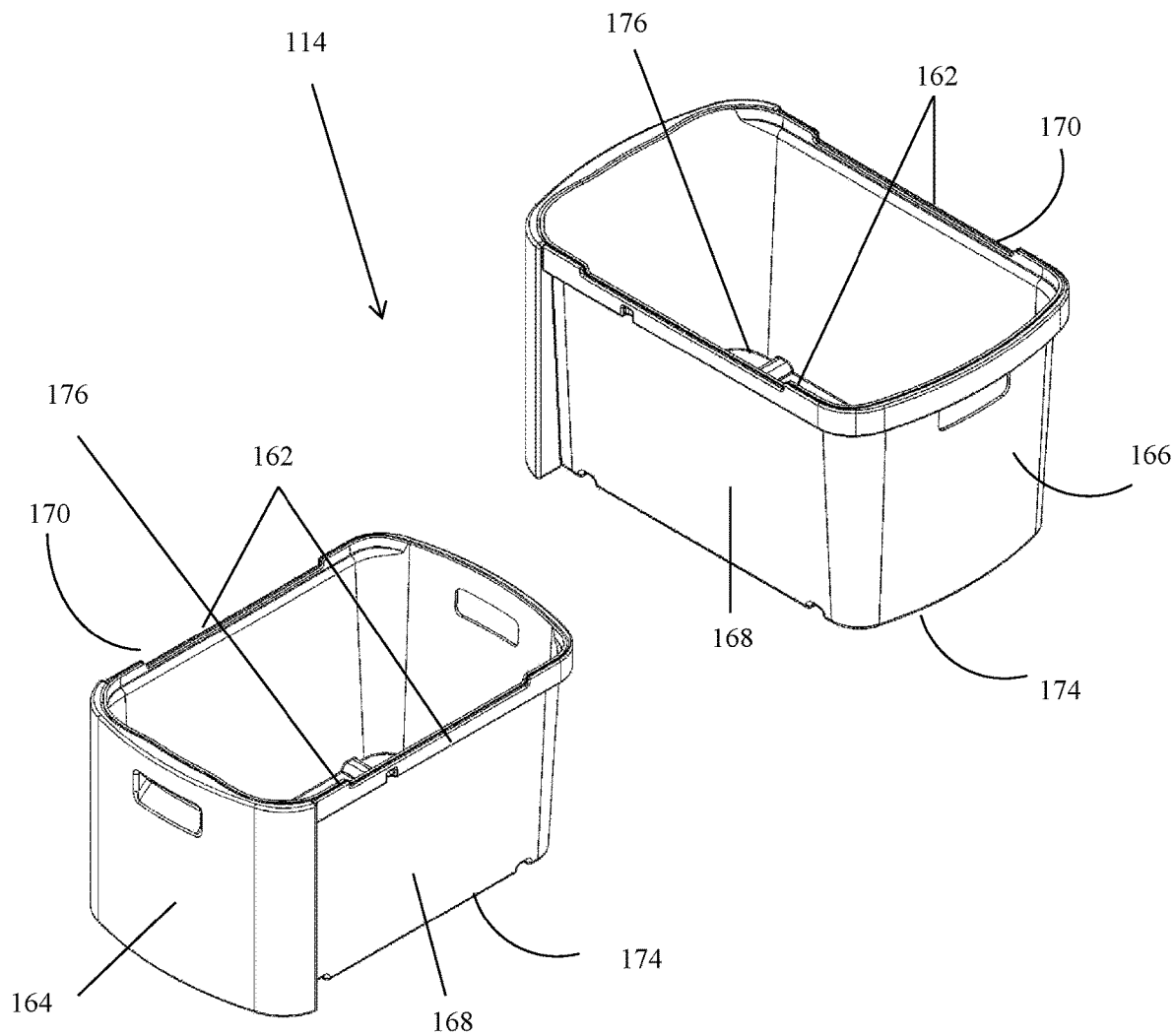
FIG. 15 shows an exemplary container that can be used for an embodiment of the robotic unit.
Figure 16:
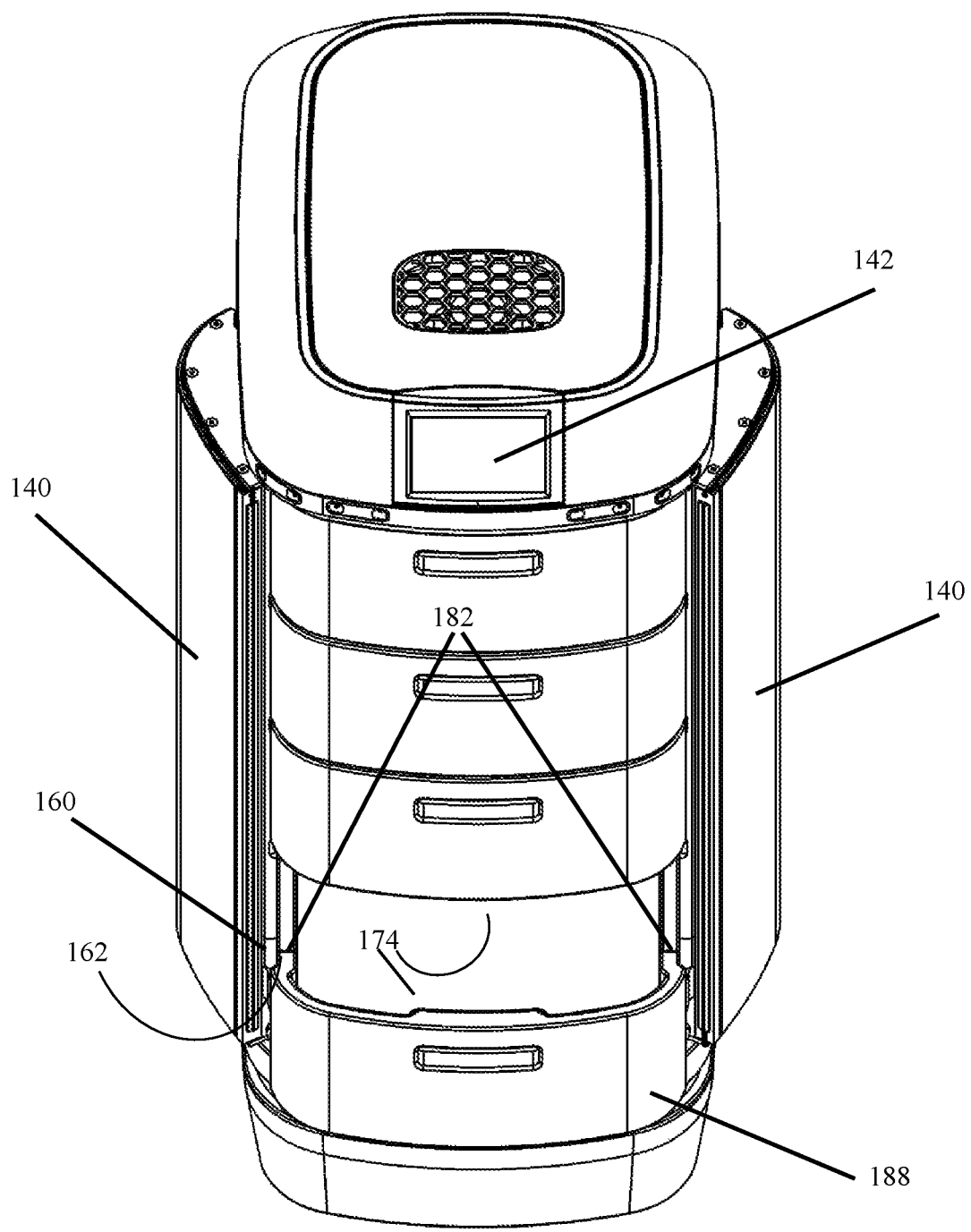
FIG. 16 shows an exemplary container arrangement that can be used for an embodiment of the robotic unit.

Referring to FIGS. 11-12, the housing 126 of the robotic unit 102 has hollowed out section defining a storage space 112. For example, the housing 126 can have an interior that is the hollowed out section with an interior bottom 148, an interior top 150, an interior rear 152, an interior first side 154, and an interior second side 156 conjoined together to form a cavity that defines the storage space 112. It is contemplated for the housing 126 to include at least one housing door 140, the back surface of which forming an interior rear 158. The storage space 112 is an area of the housing 126 that contains the items 104 and/or containers 114. In some embodiments, the storage space 112 includes at least one guide 160. The guide 160 is configured to receive a rail 162 portion of a container 114. For example, the guide 160 can be groove formed in any one or combination of the interior rear 152, interior first side 154, interior second side 156, and interior front 158. The container 114 can be configured as a tray, bin, drawer, cabinet, subcabinet, locker etc. that has a rail 162 or a lip formed about a periphery thereof, the rail 162 being configured to slide within the guide 160 and be retained in place by the mechanical engagement between the guide 160 and the rail 162.

In at least one embodiment, the guide 160 is a groove formed in the interior first side 154 and the interior second side 156, the guide 160 portion on the interior first side 154 being located at a same distance (in height) as that of the guide 160 portion on the interior second side 156. This can facilitate receiving a rail 162 located on a first side 168 of the container 114 and a rail 162 located on a second side 120 of the container 114. Some embodiments can include a plurality of guides 160. For example, a first guide 160 can be a groove formed in the interior first side 154 and the interior second side 156, the first guide 160 portion on the interior first side 154 being located at a same distance as that of the first guide 160 portion on the interior second side 156. A second guide 160 can be a groove formed in the interior first side 154 and the interior second side 156, the second guide 160 portion on the interior first side 154 being located at a same distance as that of the second guide 160 portion on the interior second side 156, wherein the first guide 160 is located at a distance that is different from that of the second guide 160. Additional guides (a third guide 160, fourth guide 160, etc.) can be used.

Referring to FIGS. 13-16, the groove in any one or combination of the guides 160 can be triangular shaped, rectangular shaped, square shaped, C-shaped, D-shaped, etc. The cross-sectional shape of the rail 162 of any one or combination of containers 114 can be triangular shaped, rectangular shaped, square shaped, C-shaped, D-shaped, etc. The cross-sectional shape of the rail 162 of any one or combination of containers 114 can be the same as or different from the shape of the grooves in the guides 160. It is contemplated for the cross-sectional shape of the rail 162 of a container 114 associated with a guide 160 to complement that of the shape of the groove for that guide 160. This can be done to facilitate slidable motion of the container 114 to and from the interior front 158 and interior rear 152 (e.g., the container 114 can be slid back and forth within the storage space 112). This can also be done to provide adequate support for the container 114 when the container 114 is slid into the guide 160 (e.g., the container 114 does move up towards the interior top 150 or down towards the interior bottom 148 when the container 114 is slide into the guide 160). When the housing door 140 is open, the container 114 is able to be slid into and out from the storage space 112.

The container 114 has a container front 164, a container rear 166, a container first side 168, a container second side 170, in some embodiments a container top 172, and a container bottom 174. The container top 172 can be open and the container front 164, container rear 166, container first side 168, container second side 170, and container bottom 174 can be conjoined to form a container receptacle 176 in which items 104 are placed. In some embodiments the contents in container 114 located in 176 will be blocked and hidden by the container bottom 174 of a container above it thereby securing the goods. In other embodiments, the container front 164 can be open and the container top 172, container rear 166, container first side 168, container second side 170, and container bottom 174 can be conjoined to form a container receptacle 176 in which items 104 are placed.

The container 114 can be configured to carry different items 114. For example, a first container 114 can be configured to carry a first type of item 104, a second container 114 can be configured to carry a second type of item 104, a third container 114 can be configured to carry a third type of item 104, etc. The engagement of the containers 114 with the guides 160 can facilitate easy re-configuration of the payload of the robotic unit 102. For example, the first container 114 can be configured as a drink holder to carry beverage type items 104, the second container 114 can be configured as a snack holder to carry snack type items 104, and the third type of container 114 can be configured as an amenities holder to carry cosmetic and toiletry type items 104. Any of the first, second, or third type containers 114 can be removed and replaced by another type of container 114 to allow the robotic unit to accommodate a specific demand for an item 104, to follow a specific delivery schedule, etc. It should be noted that the types of items 104 described above are exemplary and that other types of items 104 can be used.

As noted herein, the housing 126 can include at least one housing door 140. The housing door 140 can be hingedly attached to the housing 126 and be configured to provide selective access to the storage space 112. In at least one embodiment, the housing 126 has two housing doors 140 hingedly attached to the housing 126 in a gullwing style arrangement. For example, the housing 126 can have a first housing door 140 hingedly attached to the housing first side 128 and a second housing door 140 hingedly attached to the housing second side 130 so that when the housing doors 140 are open, they move back along the profile of the housing 126. (See FIG. 7B).

The housing door 140 includes a door lock 184. (See FIG. 13). The door lock 184 can be a mechanical lock, electrical lock, etc. For example, the door lock 184 can be an electromagnetic deadbolt that traverses a locking bolt into and out-from a deadbolt receiver based on electrical signals sent to a processor of the door lock 184. Upon the system 100 determining that the robotic unit 102 is within the designated site 106 and/or upon the system 100 identifying the individual 108 as an authorized person, the door lock 184 can open, allowing or causing the housing door 140 to open.

The processor can be programmed to unlock the door lock 184 as soon as the robotic unit 102 enters the designated area, upon receiving an authorized signal from the system 100, when an individual 108 has been property identified as being an authorized person, etc. This can be achieved by the processor of the robotic unit 102 sending a command signal to the processor of the door lock 184. The processor of the robotic unit 102 can be programmed to allow the door lock 184 to be unlocked for a predetermined amount of time (e.g., 30 seconds), until the item 104 and/or container 114 is removed, until an authorized individual indicates he/she has received the item 104 and/or container 114, etc., after which time or occurrence the processor of the robotic unit 102 causes the housing door 140 to close and the door lock 184 to lock by sending another signal to the processor of the door lock 184. For example, the processor of the robotic unit 102 may send a signal to the processor of the door lock 184 to cause it to unlock the housing door 140 and open the housing door 140 when reaching site-A 106a for 30 seconds and then close the housing door 140 and lock it regardless of the item 104 and/or container 114 being received by the intended individual 108.

Some embodiments can include a container lock 184. (See FIGS. 19-21). The container lock 184 can be configured to selectively retain the container 114 within the storage space 112. The container lock 184 can be operated based on electrical signals sent from the processor of the robotic unit 102. After the housing door 140 is unlocked and open, the system 100 can be configured to allow selective access to a certain container 114 based on the designated site 106 and/or the authorization of the individual 108. For example, upon the system 100 determining that the robotic unit 102 is within the designated site 106 the door lock 184 can open, allowing or causing the housing door 140 to open. Yet, only when the system 100 identifies the individual 108 as an authorized person, will that person be granted access to a certain container 114 by the system 100 unlocking the container lock 184 for that container 114. As will be explained, the container lock 184 can also have a processor, and the processor of the robotic unit 102 can be programmed to allow the container lock 184 to be unlocked for a predetermined amount of time (e.g., 30 seconds), after which time or occurrence the processor of the robotic unit 102 can lock the container lock 184 by sending a signal to the processor of the container lock 184.

Some containers 114 may not have a container lock 184. These can be referred to as "free containers". A free container can be a container 114 that is accessible by anyone, as long as the housing doors 140 of the robotic unit 102 are unlocked and opened. The containers 114 that are locked during a particular delivery can be referred to as "restricted containers". A restricted container can be a container 114 that is accessible only by an authorized individual 108. As a non-limiting example, upon the system 100 determining that the robotic unit 102 is within the designated site 106 the door lock 184 can open, allowing or causing the housing door 140 to open. At that time, anyone can access the free containers and the items 104 contained therein. Yet, only when the system 100 identifies the individual 108 as an authorized person, will that person be granted access to the restricted container associated with that person.

It is contemplated for the free containers 114 to include items 104 such as hotel room and bathroom products, for example, and for the restricted containers 114 to include items 104 such as beverage and snack items, for example. Hotel guests can be given an access code or token (such as, but not limited to, a room key) to allow them to open the housing door 140 of the robotic unit 102 so as to be able to access any container 114 within the robotic unit 102. This can be done to only allow hotel guests to access the containers 114 and items 104 of the robotic unit 102, thereby preventing non-guests from accessing the contents of the robotic unit 102.

It should be noted that a plurality of access codes or tokens can be used. For instance, an access code or token can be used to access the housing door 140 and an access code or token can be used to access a container 114. The access code or token used to access the housing door 140 can be the same as or different form the access code or token used to access the container 114. In addition, as there can be a plurality of containers 114, there can be a separate access code or token for accessing each, or any combination, or containers 114.

As a non-limiting example, the system 100 can be configured for use in a hospitality setting (e.g., a hotel). The robotic unit 102 can have a plurality of first type containers 114 carrying various beverage items (e.g., the first type containers 114 can have drink holders). The robotic unit 102 can have a plurality of second type containers 114 carrying various snack food items (e.g., the second type containers can have snack holders). The robotic unit 102 can have a plurality of third type containers 114 carrying various hotel room and bathroom products, such as cosmetics, toiletries, towels, etc. As the robotic unit 102 roams about the hotel or follows a predetermined path, items 104 can be accessed or delivered to hotel guests and staff. Any of the first, second, or third type containers 114 can be removed and replaced by another type of container to allow the robotic unit 102 to accommodate a specific demand for an item 104, to follow a specific delivery schedule, etc.

For instance, the robotic unit 102 can be configured for use as a vending unit. In this case, the robotic unit would have a plurality of first type containers 114 carrying drinks and second type containers 114 carrying snacks. Each of the first and second type containers 114 can be locked (i.e., restricted) so as to only be accessed by a user (e.g., a hotel guest) who enters an access code. For example, hotel guest can be given an access code or token when registering with the hotel. This access code can allow them open the housing door 140 (e.g., unlock the housing door 140) of the robotic unit 102 and/or gain access to any container 114 (unlock the container(s) 114) within the robotic unit 102. In this situation, the chain of custody tracking feature can be initiated as soon as the container 114 has been unlocked via input of an access code. The chain of custody information can track whether an item 104 has been removed from the container 114, which container 114 has been accessed, the time and location the container 114 was accessed, the time and location the item 104 was moved, which individual removed an item 104 from a specific container 114, etc.

As another example, the robotic unit 102 can be made to travel throughout a hotel with a plurality of lockable containers 114, each container 114 configured to carry an order of food 104 (e.g., food ordered via room service or outside delivery service). The robotic unit 102 travels to room-1 designated as a location for delivery of food order-1. The hotel guest of room-1 can enter his/her access code and be allowed to access container-1 to retrieve food order-1, but cannot access any other container 114 within the robotic unit 102. The robotic unit travels to room-2 designated as a location for delivery of food order-2. The hotel guest of room-2 can enter his/her access code and be allowed to access container-2 to retrieve food-order-2, but cannot access any other container 114 within the robotic unit 102.

As another non-limiting example, the robotic unit 102 can be made to travel throughout a hospitality setting (e.g., hotel) with a kit of supplies used for housekeeping with a plurality of non-locking containers filled with materials needed for room cleaning and turnover including supplies and linens. The robotic unit 102 travels to room-1 designated as the assigned room for turnover. The housekeeper accesses the payload and removes pre-filled containers. The housekeeper then fills the robot with the used linens where it returns to a central processing location in the hotel.

As another non-limiting example, the robotic unit 102 can be made to travel throughout a residential setting (e.g., an apartment complex, a condominium complex, etc.) with a plurality of lockable containers 114, each container 114 configured to carry a parcel 104 or package. The robotic unit 102 travels to apartment-1 designated as a location for delivery of parcel-1. The apartment resident of apartment-1 can enter his/her access code and be allowed to access container-1 to retrieve parcel-1, but cannot access any other container 114 within the robotic unit 102. The robotic unit 102 travels to apartment-2 designated as a location for delivery of parcel-2. The apartment resident of apartment-2 can enter his/her access code and be allowed to access container-2 to retrieve parcel-2, but cannot access any other container 114 within the robotic unit 102.

In some embodiments, the robotic unit 102 will not grant access to the item 104 unless the robotic unit 102 is at the designated location and the correct access code is received. In other words, the user has to be at the delivery location and enter the correct access code in order to gain access to the container 114. For instance, the apartment resident of apartment-1 must be located at apartment-1 and enter his/her access code to be allowed to access container-1 to retrieve parcel-1.

As another example, the system 100 can be configured for use in a hospital setting, in which the free containers include items 104 such as foodstuff, toiletries, other supplies, etc., and the restricted containers include items 104 such as medicine, drugs, medical sharps, medical diagnosis, etc. Thus, selective or discriminatory access may be desired.

Using the delivery schemes disclosed herein can be beneficial in that the robotic unit 102 can make multiple types of deliveries (some items 104 being restricted to being accessed by authorized individuals 108 and some items 104 being freely accessed) by following a single delivery schedule or delivery route 110. In contrast, conventional systems and methods require use of delivery units and delivery routes 110 to deliver restricted items that are separate and distinct from delivery units and delivery routes 110 to deliver freely accessible items.

The details of the container lock 184 will be discussed later, but the container lock 184 is configured to hold the container 114 in a stowed position 186 until the container lock 184 is unlocked. A stowed position 186 is one in which the container 114 is held within the storage space 112 so that the container 114 cannot be removed from the storage space 112. (See FIG. 13). The stowed position 186 is also one in which the container rails 162 and container rim 182 are slidingly engaged with the guides 160 and the container 114 is located within the storage space 112 so that the contents are protected by the bottom 174 of the upper container. In this regard, the container 114 is held in place at a location that prevents the contents to be seen or accessed. One cannot access the items 104 within the container 114 when the upper container is the container 114.

The container 114 can be unlocked via the container lock 184 and slid out to an un-stowed position 188. In addition, in certain embodiments the container 114 can be slid completely out from the storage space 112.

Figure 17A:
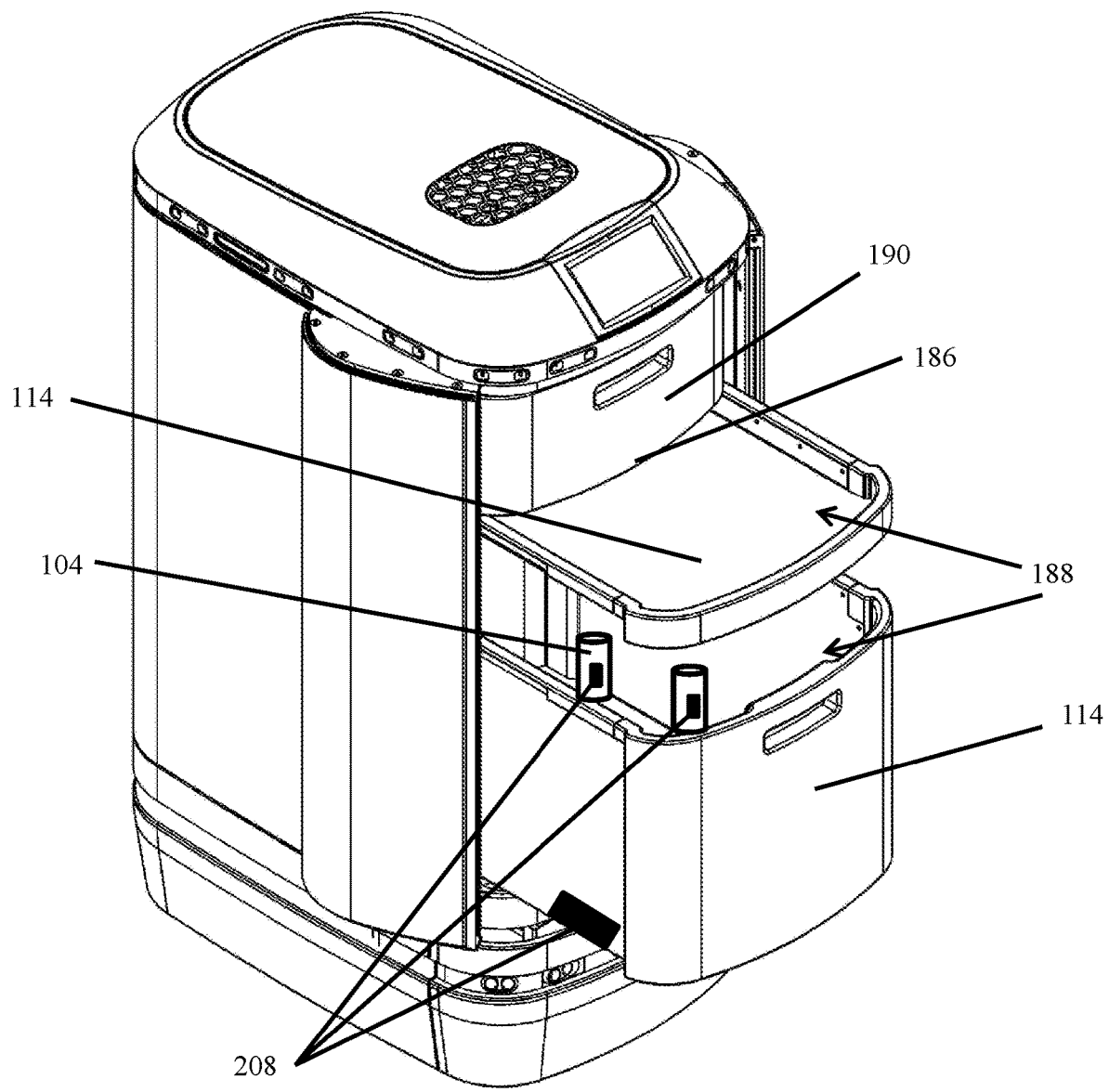
FIG. 17A shows an exemplary container and locker-door configuration with the locker-door in a closed position.
Figure 17B:
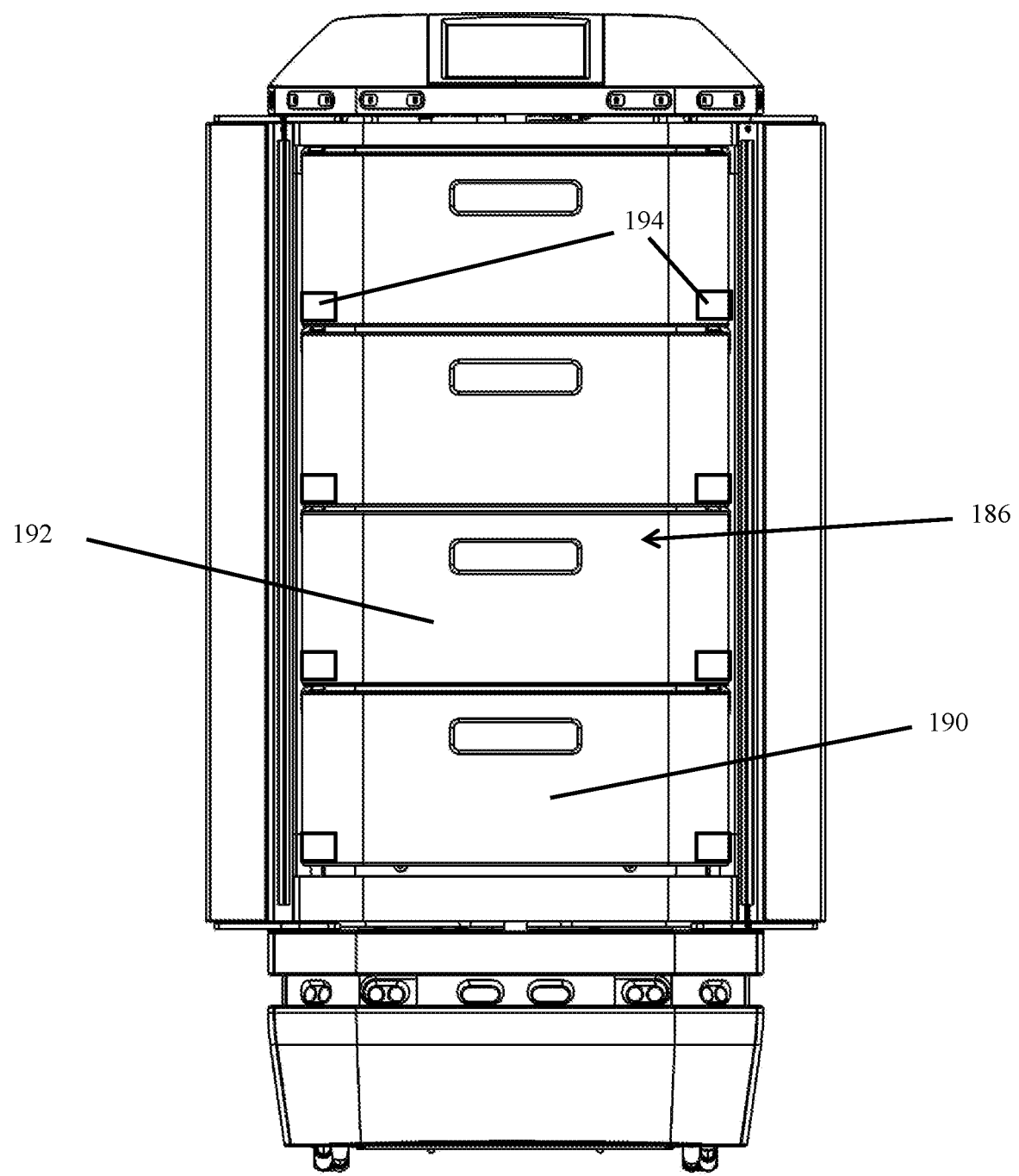
FIG. 17B shows another exemplary container and locker-door configuration with the locker-door in a closed position.
Figure 17C:
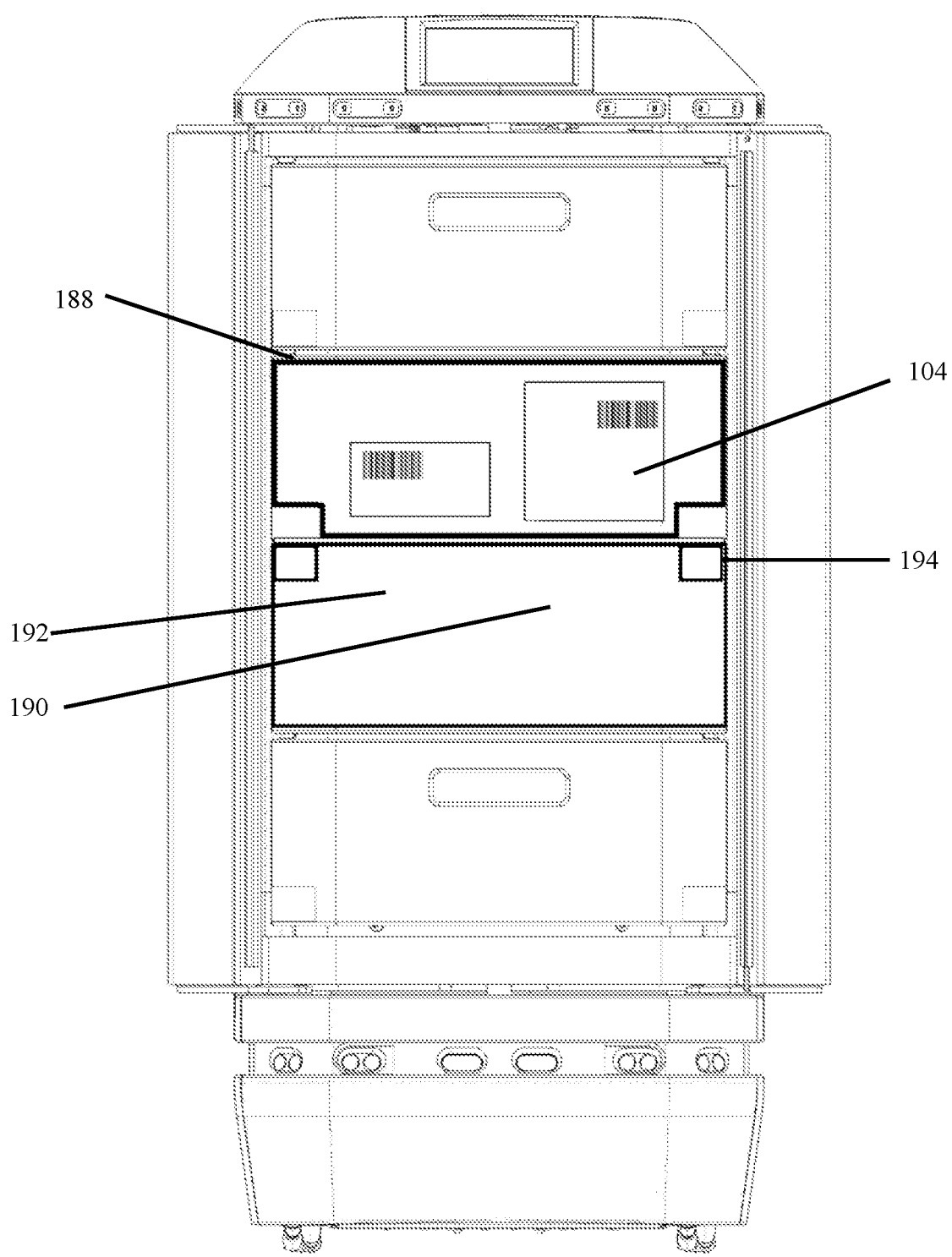
FIG. 17C shows an exemplary container and locker-door configuration with the locker-door in an open position.
Figure 18:
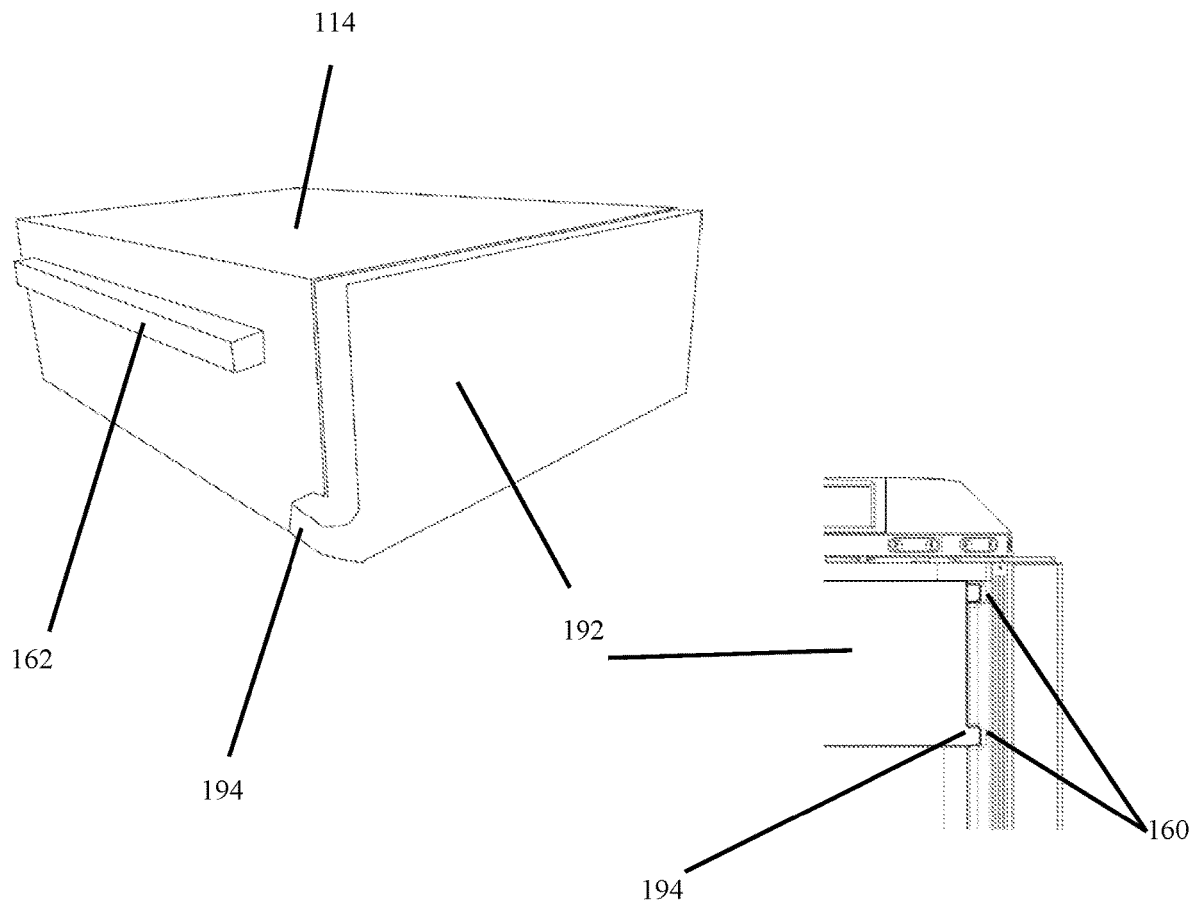
FIG. 18 shows an exemplary locker-door configuration that can be used with an embodiment of the robotic unit.

Referring to FIGS. 17-18, in addition to or in alternative to the container 114 the container 114 can have a locker-door 190. The locker-door 190 is hingely attached to the container front 164. For example, the locker-door 190 can be hingely attached to the container front 164 at or near the container bottom 174 so that the locker-door 190 swings open by rotating down towards the container bottom 174 and swings closed by rotating up towards the container top 172. The locker-door 190 can be a planar member 192 with at least one guide tab 194. The guide tab 194 can be a protrusion that is configured to slidingly engage a guide 160. For example, the cross-sectional shape of the guide tab 194 can complement that of the shape of the groove for a guide 160, allowing the guide tab 194 to slidingly engage the guide 160. In this regard, the cross-sectional shape of the guide tab 194 can be triangular shaped, rectangular shaped, square shaped, C-shaped, D-shaped, etc. It is contemplated for the cross-sectional shape of the guide tab 194 to have an angle (e.g., be square shaped, triangular shaped, etc.) and for the shape of the groove of the guide 160 to be the same as that of the cross-sectional shape of the guide tab 194. This can be done to allow the guide tab 194 to slidingly engage the guide 160 when the guide tab 194 is in an orientation that causes the shape profile of the guide tab 194 to match that of the guide 160 but prevents sliding engagement when the guide tab 194 is in an orientation that causes the shape profile of the guide tab 194 to not match that of the guide 160. For example, if the cross-sectional shape of the guide tab 194 is square and the groove of the guide 160 is square, the guide tab 194 can only slidingly engage the guide 160 if the guide tab 194 is orientated so that its shape profile matches the shape profile of the guide 160. This can also be done to require the locker-door 190 to be rotated to a certain position to allow the guide tab 194 to slidingly engage the guide 160. For example, the locker-door 190 may have to be rotated up to a closed position before the guide tab 194 can slidingly engage the guide 160. In addition, the locker-door 190 cannot be rotated down to an open position unless the guide tab 194 is disengaged from the guide 160. For example, with the locker-door 190 hingely attached to the container front 164, the container 114 may have to be slid out (at least partially) from the storage space 112 to cause the guide tab 194 to disengage from the guide 160 and allow the locker-door 190 to be rotated to the open position. Otherwise, the locker-door 190 is locked in the closed position by the inability to rotate the locker-door 190 open.

As noted herein, the container lock 184 can be used to hold the container 114 in a stowed position 186. With embodiments of the container 114 having a locker-door 190, the stowed position 186 can be defined as the container 114 being slid into the storage space 112 so that the guide tab 194 is slidingly engaged with the guide 160. This can include the locker-door 190 being rotated to the closed position. The locker-door 190 cannot be opened (e.g., cannot be rotated to the open position) when the locker-door 190 is rotated to the closed position and the container 114 is slid into the storage space 112 so that the guide tab 194 is slidingly engaged with the guide 160. With container lock 184 holding the container 114 in the stowed position 186 until the container lock 184 is unlocked, no access to the items 104 within the container 114 can be obtained.

The guide tab 194 for the locker-door 190 can be positioned on the locker-door 190 to engage the same guide 160 as the container rail 162 or to engage a guide 160 that is different from the guide 160 that the container rail 162 engages. For example, the locker-door 190 can have a guide tab 194 extending from a side at or near a top of the locker-door 190 so that the guide tab 194 engages the same guide 160 as the container rail 162. In addition, or in the alternative, the locker-door 190 can have a guide tab 194 extending from a side at or near a bottom of the locker-door 190 so that the guide tab 194 engages a guide 160 that is different from the guide the container rail 162 engages. In some embodiments, the locker-door 190 has a plurality of guide tabs 194. For example, the locker-door 190 can have at least one first guide tab 194a extending from a first side of the locker-door 190. The locker-door 190 can have at least one second guide tab 194b extending from a second side of the locker-door 190.

Figure 19:
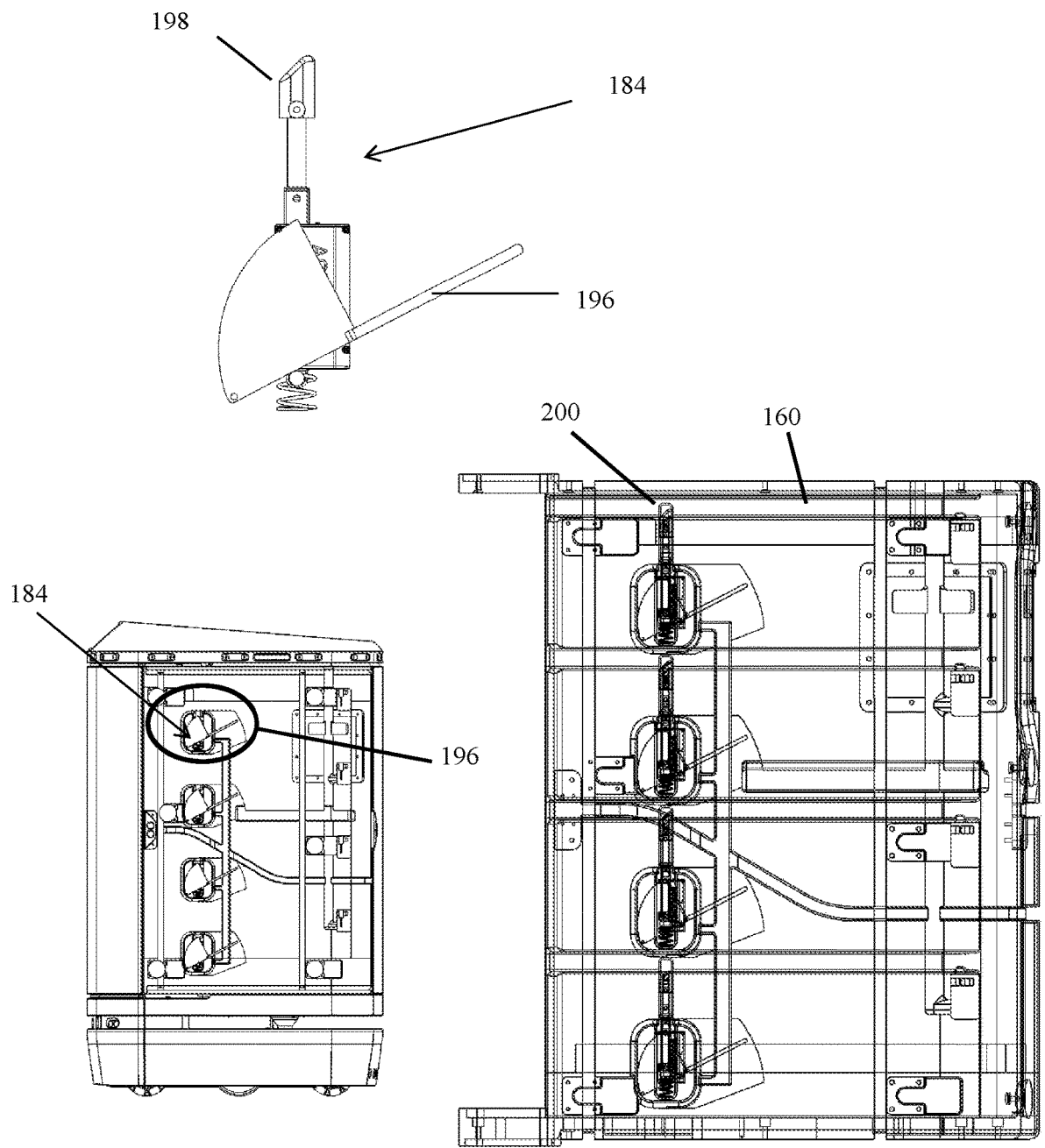
FIG. 19 shows an exemplary container lock configuration with a lever and catch arrangement that can be used with an embodiment of the robotic unit.

Referring to FIG. 19, in one embodiment, the container lock 184 can be a lever 196 having a catch 198, the lever 196 being attached to an electromechanically actuated spring-plunger 210. The container lock 184 can be attached to a portion of the container 114 (e.g., at or near the container rail 162) and/or a portion of the housing 126 (e.g., at or near a guide 160). In one embodiment, the container lock 184 is attached to the housing first side 128 and/or housing second side 130 so that the catch 198 is able to extend through a notch 200 formed within a guide 160. The container rail 162 has a corresponding notch 200 that co-registers (e.g., spatially aligned with each other) with the notch 200 of the guide 160 when the container 114 is in a stowed position 186. When co-registered, the lever 196 can be caused to pivot via the motor to position the catch 198 so that it engages the notches 200, thereby locking the container 114 in the stowed position 186. The lever 196 can be can be caused to pivot via the motor to position the catch 198 so that it dis-engages from the notches 200, thereby unlocking the container lock 184 and allow the container 114 to be slid within the guides 160. This can include sliding the container 114 away from the interior rear 152 and into the un-stowed position 188.

The motor of the container lock 184 can have a processor that receives signals from the processor of the robotic unit 102. Upon the system 100 determining that the robotic unit 102 is within the designated site 106 and upon the system 100 identifying the individual 108 as an authorized person, the container lock 184 can open, allowing the container 114 to be freely slid within the guides 160. This can include sliding the container 114 from its stowed position 186 so that the container lid 178 can be lifted or swung open. This can include sliding the container 114 from its stowed position 186 so that the locker-door 190 can be rotated to an open position. When the container 114 is slid back to its stowed position 186, a signal from the processor of the robotic unit 102 can be sent to the processor of the motor to cause the catch 198 of the lever 196 to engage the notches 200 and lock the container 114 in the stowed position 186.

Figure 20:
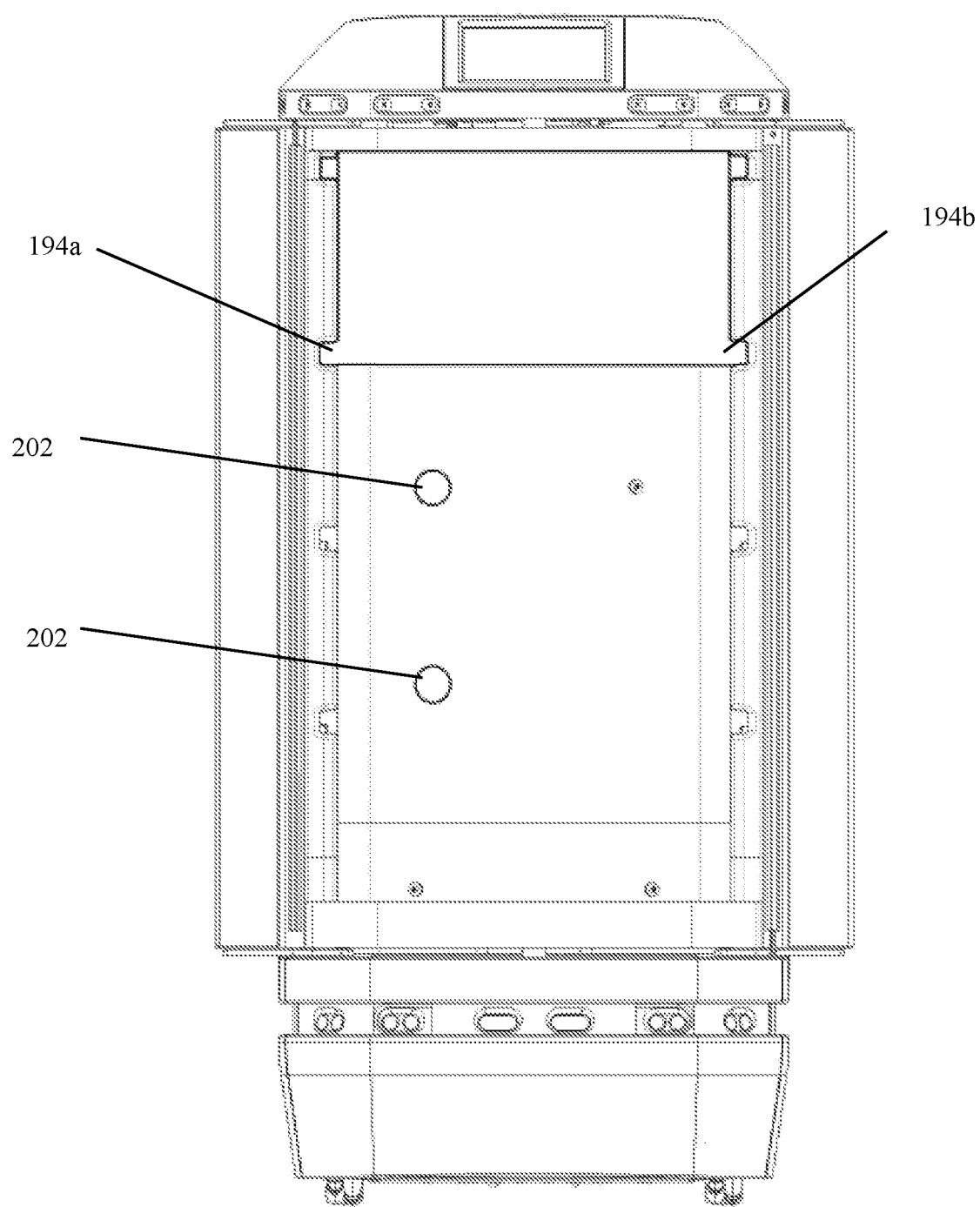
FIGS. 20-21 show an exemplary container lock configuration with magnet arrangement that can be used with an embodiment of the robotic unit.
Figure 21:
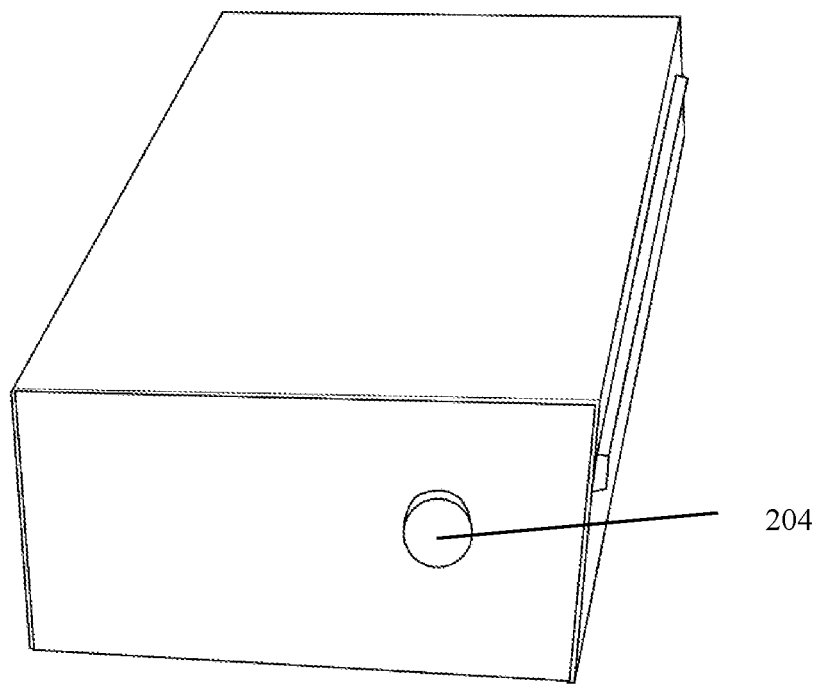

Referring to FIGS. 20-21, in addition or in the alternative to the container lock 184 being a lever arrangement, the container lock 184 can be a magnet arrangement. The magnet arrangement can be at least one first magnetic element 202 disposed on the housing interior and at least one second magnetic element 204 disposed on the container 114.

The first magnetic element 202 can be disposed on the interior rear 152, an interior first side 154, an interior second side 156, within a guide 160, etc. The second magnetic element 204 can be disposed on the container rear 166, container first side 168, container second side 170, container rail 162, etc. The first magnetic element 202 can be a magnet or a material attractable by magnetic force. The second magnetic element 204 can be a magnet or a material attractable by magnetic force. It is contemplated for at least one of the first magnetic element 202 and the second magnetic element 204 to be a magnet. Any of the magnets of the first magnetic element 202 and/or the second magnetic element 204 can be an electromagnet, allowing the magnet to be electively magnetized.

The first magnetic element 202 and the second magnetic element 204 are positioned so that when the container 114 is slid into the storage space 112 and slid into a stowed position 186, the first magnetic element 202 and the second magnetic element 204 co-register. When the electromagnet of the first magnetic element 202 and/or the second magnetic element 204 is magnetized and the first magnetic element 202 and the second magnetic element 204 are co-registered, the magnetic force causes the first magnetic element 202 and the second magnetic element 204 to attract. This attraction force is the locking mechanism of the container lock 184 and prevents the container 114 from being slid to or from the interior rear 152 and/or interior front 158. This can include locking the container in the stowed position 186.

The electromagnet of the first magnetic element 202 and/or the second magnetic element 204 can have a processor that receives signals from the processor of the robotic unit 102. Upon the system 100 determining that the robotic unit 102 is within the designated site 106 and upon the system 100 identifying the individual 108 as an authorized person, the container lock 184 can open, allowing the container 114 to be freely slid within the guides 160. This can include sliding the container 114 from its stowed position 186 so that the container lid 178 can be lifted or swung open. This can include sliding the container 114 from its stowed position so that the locker-door 190 can be rotated to an open position. When the container 114 is slid back to its stowed position 186, a signal from the processor of the robotic unit 102 can be sent to the processor of the electromagnet to cause the first magnetic element 202 and the second magnetic element 204 to attract and lock the container 114 in the stowed position 186.

In some embodiments the container 114 can be configured as a drawer that slides in and out of the storage space 112. The actuation of the drawer-type container 114 can be manual or via a mechanical motor (e.g., a solenoid actuator). In some embodiments, the drawer-type container 114 can be affixed in place within the storage space 122 and have a door that is open and closed via actuation of a solenoid actuator, while the container 114 remains affixed in place within the storage space 112.

Figure 22:
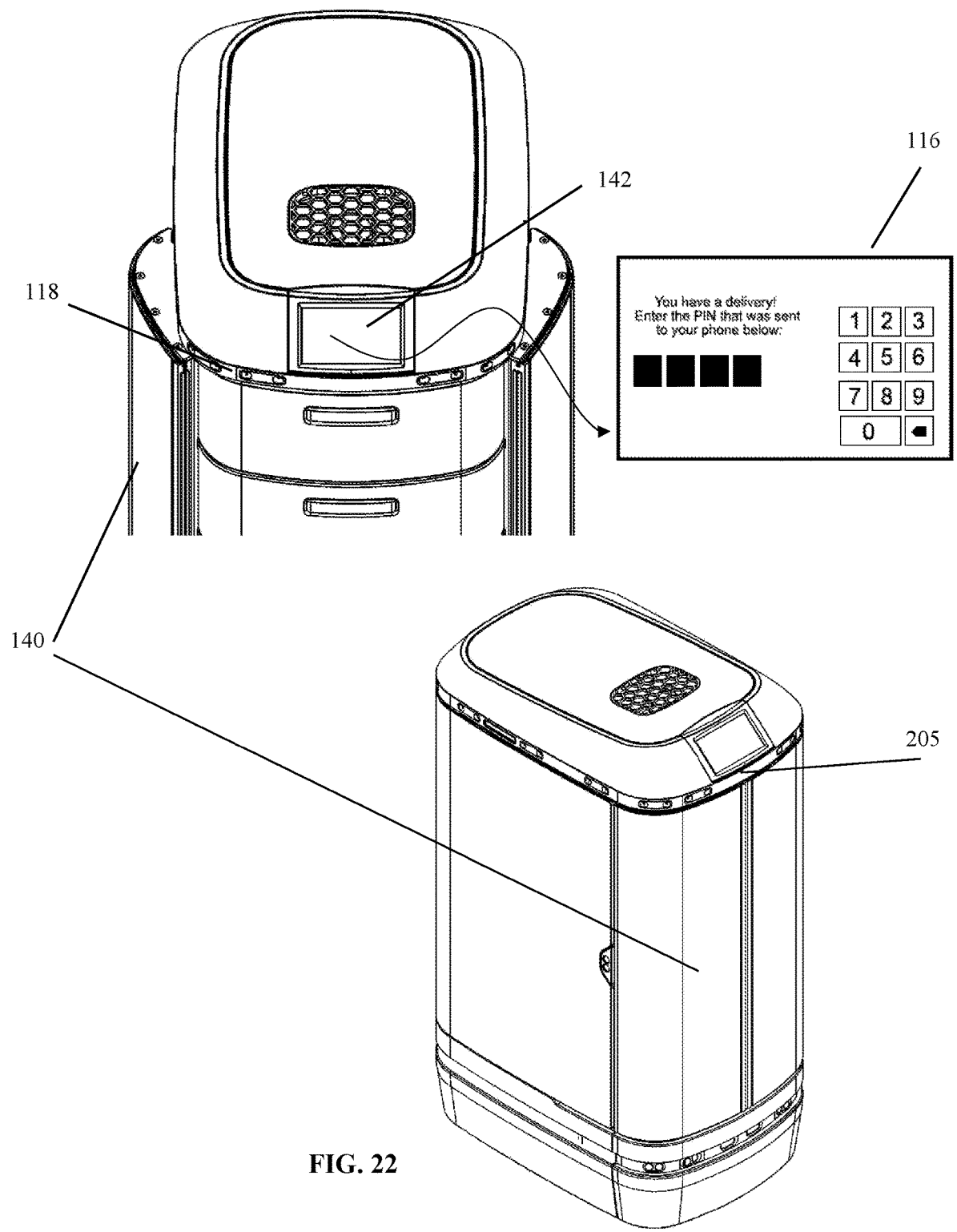
FIG. 22 shows an exemplary user interface that can be used with an embodiment of the system.

Referring to FIG. 22, the robotic unit 102 can include a display 142 configured to display a user interface 116. The user interface 116 can be programmed to facilitate control of and display of various operational aspects of the robotic unit 102. The user interface 116 includes interactive elements to allow a user to enter information that allows the user to open and close the housing door 140, lock and unlock the container lock 184, validate that the site 106 is the correct site 106, validate that the user is an authorized individual 108, etc.

As noted above, any of the robotic unit sensors 118 can be a scanner, and thus the user interface 116 can request that a user scans a token of various types (such as a room key), the token being associated with the site 106, to validate that the robotic unit 102 is at the correct site 106 before opening the housing door 140 and/or unlocking the container lock 184. Other means for entering validation information such as a pin code can be used.

Upon entering the validating information, the processor of the robotic unit 102 analyzes the information to determine if the site 106 is the correct site 106. If the site 106 is the correct site 106, the processor of the robotic unit 102 sends a signal to the processor of the door lock 184 to unlock the door lock 184 and/or sends a signal to the processor of the container lock 184 to unlock the container lock 184.

As another example, the user interface 116 can request that a user enters a code, a personal identifier, etc. to validate that the user is an authorized individual 108 before opening the housing door 140 and/or unlocking the container lock 184. As any of the robotic unit sensors 118 can be a scanner, the user interface 116 can request that a user scans a token, the token being associated with the user, to validate that the user is an authorized individual 108 before opening the housing door 140 and/or unlocking the container lock 184. As noted above, any of the robotic unit sensors 118 can be a biometric scanner, and thus the user interface 116 can request that a user scans a portion of his/her body (such as finger) to validate that the user is an authorized individual 108 before opening the housing door 140 and/or unlocking the container lock 184. Other means for entering validation information can be used.

Upon entering the validating information, the processor of the robotic unit 102 analyzes the information to determine if the user is an authorized individual 108. If the user is an authorized individual 108, the processor of the robotic unit 102 sends a signal to the processor of the door lock 205 and/or sends a signal to the processor of the container lock 184 to unlock the container lock 184

As noted herein, the robotic unit 102 can be configured to hold a plurality of containers 114. A container 114 can be encoded when placed in the storage space 112 so that when its second magnetic element 204 co-registers with a corresponding first magnetic element 202, the system 100 can identify that container 114. As another example, a container 114 can be encoded when placed in the storage space 112 so that when its container lock 184 locks due to the co-registration of the catch 198 and the notches 200, the system 100 can identify that container 114.

As a non-limiting example, the encoding can be achieved via coordinated communication between the container lock 184 of the container 114 and the processor of the robotic unit 102. A container 114 can hold designated items 104 for a designated purpose (e.g., for vending). If a container 114 is designated for such a purpose, only individuals who have been given an access code or a token for access to that container 114 can access the container 114. For instance, a first container 114 can hold items 104 designated for purchase by a first set of individuals 108 (e.g., registered guests of a hotel), a second container 114 can hold items 104 designated for delivery to a second set of individuals (e.g., registered guest of the hotel who ordered room service), and a third container 114 can hold items 104 designated for delivery to a third set of individuals (e.g., hotel staff). Anyone of the first, second, and third set of individuals can open the housing door 140 via entry of an access code or token to identify them as guests or staff of the hotel so as to access the items 104 of the second container 114. However, the first container 114 can be locked via the container lock 184 until any one of the first set of individuals 108 enters validating information to cause the processor of the robotic unit 102 to send a signal that opens the container lock 184 for the first container 114. Similarly, the second container 114 can be locked via the container lock 184 until any one of the second set of individuals 108 enters validating information to cause the processor of the robotic unit 102 to send a signal that opens the container lock 184 for the first container 114. Additionally, the third container 114 can be locked via the container lock 184 until any one of the third set of individuals 108 enters validating information to cause the processor of the robotic unit 102 to send a signal that opens the container lock 184 for the third container 114.

For the scenario in which the robotic unit 102 is delivering items 104 for specific individuals (e.g., delivery of room service items, delivery of parcels to apartment residents, etc.), each container 114 can hold designated items 104 for a designated individual 108. If a container 114 is designated for such a purpose, only an authorized individual 108 for whom the designated items 104 are intended for can access that container 114. Thus, an identified container 114 can be designated for holding designated items 104 for a designated individual 108. For instance, a first container 114 can hold items 104 designated for a first individual 108, a second container 114 can hold items 104 designated for a second individual 108, a third container 114 can hold items 104 that are not designated for any individual 108. The first container 114 can be locked via the container lock 184 until the first individual 108 enters the validating information to cause the processor of the robotic unit 102 to send a signal that opens the door 140 and unlocks container lock 184 for the first container 114. The second container 114 can be locked via the container lock 184 until the second individual 108 enters the validating information to cause the processor of the robotic unit 102 to send a signal that opens the door 140 and container lock 184 for the second container 114. The third container 114 can remain unlocked and can be freely accessed by any individual 108 at any time the door lock 184 is unlocked.

The user interface 116 can also include interactive elements to facilitate tracking chain of custody for the items 104 and/or containers 114. For example, the user interface 116 can request that a user identify the items 104 that had been removed from the container 114 after the container 114 has been accessed. In addition, or in the alternative, the processor of the robotic unit 102 can track the routes 110 taken by the robotic unit 102, the time it takes to make the deliveries, the time the robotic unit 102 stops at each site 106, the amount of time the robotic unit 102 stops at each site 106, the correct and/or incorrect validating information entered into the user interface 116 or received by the processor of the robotic unit 102 via the robotic sensors 118, which containers 114 were accessed at each site 106, the individuals 108 accessing the containers 114 at each site 106, etc.

In some embodiments, the items 104 and/or can have tracking markers 208 attached to them. (See FIG. 17A). These can be sensed by any one or combination of the robotic unit sensors 118. This can be done to determine if and when the item 104 and/or container 114 exits the storage space 112. For example, any one or combination of robotic unit sensors 118 can be placed within the storage space 112 and can continuously, periodically, or at the discretion of the user (e.g., via the user interface 116) scan for the items 104 and/or containers 114. In addition, or in the alternative, the user interface 116 can request that a user identified him/herself and then scan an item 104 via a robotic unit sensor 118 located on an outside surface of the robotic unit 102.

This can be done to identify the individual 108 who has removed the item 104. The system 100 can be configured so that if the user does not scan the item 104 within a predetermined time period after the robotic unit 102 detects the item 104 being removed from the storage space 112, the robotic unit 102 can transmit an alert signal (e.g., transmit an alert signal to a computer device 124), sound an audible alarm, close and lock the housing door 140, etc.

As noted above, the robotic unit 102 can be part of or in connection with a communications network 122. (See FIG. 4). For example, the processor of the robotic unit 102 can include switches, transmitters, transceivers, routers, gateways, etc. to facilitate communications via a communication protocol that facilitates controlled and coordinated signal transmission and processing. The communication links can be established by communication protocols that allow a robotic unit 102 to form the communications network 122 with another robotic unit 102 and/or another apparatus (e.g., a computer device 124). Embodiments of the computer device 124 can include a server, a mainframe computer, a desk top computer, a laptop computer, a tablet, a smartphone, etc. Any one or combination of the other robotic unit 102 and/or computer device 124 can be on the same communications network 122 or a different communications network 122. For instance, the robotic unit 102 can be configured to communicate with another robotic unit 102 and/or computer device 124 and to facilitate data transmissions to and from nodes (e.g., robotic units 102 or computer devices 124) within or between discrete communication networks. The communications network 122 can be a long range wired or a wireless network, such as an Ethernet, telephone, Wi-Fi, Bluetooth, wireless protocol, cellular, satellite network, cloud computing network, etc. Embodiments of the communications network 122 can be configured as a predetermined network topology. This can include a mesh network topology, a point-to-point network topology, a ring (or peer-to-peer) network topology, a star (point-to-multiple) network topology, or any combination thereof.

In addition, robotic unit 102 can have an application programming interface (API) and/or other interfaces configured to facilitate a computer device 124 that is in communication with the robotic unit 102 executing commands and controlling aspects of the robotic unit 102. For example, the computer device 124 can be programmed to generate a user interface 116 configured to facilitate control of and display of various operational aspects of the robotic unit 102. In addition, the user interface 116 of the computer device 124 can be programmed to display statistics and other analytics regarding the chain of custody information.

An exemplary implementation of the system 100 includes placing item-A 104*a* in container-A 114*a*, item-B 104*b* in container-B 114*b*, and item-C 104*c* in container-C 114*c*. Item-A 104*a* is designated for delivery to individual-A 108*a* (or designated for the purpose of delivering to set of individual-A's), item-B 104*a* is designated for delivery to individual-B 108*b* (or designated for the purpose of delivering to set of individual-A's), and item-C 104*a* is not designated for delivery to any particular individual 108 (or not designated for the purpose of delivering to any particular set of individuals). The containers 114*a*, 114*b*, 114*c* are placed within the storage space 112. Container-A 114*a* is locked via its container lock 184*a* and is registered as a restricted container only to be accessed by individual-A 108*a* (or any individual from the set of individual-A's). Container-B 114*b* is locked via its container lock 184*b* and is registered as a restricted container only to be accessed by individual-B 108*b* (or any individual from the set of individual-A's). Container-C 114*b* is not locked and is registered as a free container to be accessed by any individual 108. The housing doors 140 are locked via the door lock 184.

In one exemplary implementation, the robotic unit 102 is caused to follow a generally determined or predetermined path 110 throughout the facility (e.g., hotel). This can involve any one or combination of roaming about the hotel by following predetermined paths dictated by a map of the hotel, making specific deliveries to specific locations, making specific deliveries to specific individuals, etc. For instance, the robotic unit 102 can be cause to deliver item 104*a* to individual-A 108*a* located a room 123. The robotic unit 102 then navigates the predetermined path 110 and takes any detours that it is instructed to take via the computer device 124 and/or calculated to take by data acquisition of the surroundings. On its way, individual-B 108*b* stops the robotic unit 102 to access item 104*b* from the container-B upon the robotic unit 102 receiving validating information from individual-B 108*b*. The robotic unit 102 navigates to room 123 and receives validating information that it is located at room 123 (e.g., the robotic unit 102 determines it is at room 123 by comparing its location with the map). Individual-A accesses item 104*a* from container-A upon the robotic unit 102 receiving validating information from individual-A 108*a*. The robotic unit 102 then continues to roam about the hotel to be stopped by individual-C located at the lobby area. Individual-C accesses item 104*c* from container-C upon the robotic unit 102 receiving validating information from individual-C 108*a* that individual-C is a guest of the hotel.

In some embodiments, the robotic unit 102 can be configured to not stop between delivery sites. Thus, the robotic unit 102 may be caused to deliver item-A 104*a* to individual-A 108*a* without being able to be stopped by individual-B 108*b*.

In another exemplary implementation, the robotic unit 102 is caused to follow a generally determined or predetermined path 110 throughout the facility to deliver item 104*a* to individual-A 108*a* located at site-A 106*a* and to deliver item 104*b* to individual-B 108*b* locate at site-B 106*b*. The robotic unit 102 navigates the path 110 and takes any detours that it is instructed to take via the computer device 124 and/or calculated to take by data acquisition of the cameras/sensors 120 and data acquisition of the environment scan. The robotic unit 102 navigates to site-A 106*a* and receives validating information that it is within site-A 106*a*. The robotic unit 102 then unlocks the housing doors 140 to grant access to the storage space 112. Any individual 108 can remove container-C 114*c* and/or item-C 104*c*. Only upon receiving validating information from individual-A 108*a* does the robotic unit 102 unlock container lock 184*a* to allow individual-A 108*a* to gain access to container-A 114*a* and/or item-A 104*a*. The robotic unit 102 records the items 104 and/or containers 114 accessed and the individuals 108 accessing those items 104 and/or containers 114. The robotic unit 102 closes the housing doors 140 and locks the door lock 184. The robotic unit 102 navigates to site-B 106*b* and receives validating information that it is within site-B 106*b*. The robotic unit 102 then unlocks the housing doors 140 to grant access to the storage space 112. Any individual 108 can remove container-C 114*c* and/or item-C 104*c*. Only upon receiving validating information from individual-B 108*a* does the robotic unit 102 unlock container lock 184*b* to allow individual-B 108*a* to gain access to container-B 114*a* and/or item-A 104*b*. The robotic unit 102 records the items 104 and/or containers 114 accessed and the individuals 108 accessing those items 104 and/or containers 114. The robotic unit 102 closes the housing doors 140 and locks the door lock 184.

With any implementation, the system 100 can be configured to track a chain of custody for any item 104. Any time the item 104 has been moved from its location within a container 114, the system 100 can record the time and place the item 104 was moved, as well as the individual who currently had access to the robotic unit 102 and/or container 114.

With any implementation, the robotic unit 102 can be re-configured by removing and replacing any container 114 type with another container 114 type. For example, the robotic unit 102 can include containers 114 specifically configured for delivery of items 104 in the lobby area of the hotel and then be re-configured to deliver items 104 in the back-office area of the hotel, and then be re-configured to deliver items 104 in the kitchen area, etc.

Additional understanding of the disclosed system and methods of use can be obtained from the materials attached as an appendix of this specification.

It should be understood that the disclosure of a range of values is a disclosure of every numerical value within that range, including the end points. It should also be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

It should be understood that modifications to the embodiments disclosed herein can be made to meet a particular set of design criteria. For instance, any of the robotic units 102, containers 114, robotic unit sensors 118, camera/sensors 120, communication networks 122, computer devices 124, container locks 184, tracking markers 208, and/or other components of the system 100 can be any suitable number or type of each to meet a particular objective. Therefore, while certain exemplary embodiments of the system 100 and methods of using the same disclosed herein have been discussed and illustrated, it is to be distinctly understood that the invention is not limited thereto but may be otherwise variously embodied and practiced within the scope of the following claims.

What is claimed is:

1. A delivery and chain of custody system, comprising:
    a robotic unit configured to follow a determined or predetermined route throughout a facility to deliver items, the robotic unit comprising a processor and a housing having an interior bottom, an interior top, an interior rear, an interior first side, and an interior second side conjoined together to form a cavity that defines a storage space, the storage space configured to receive a plurality of modular containers of different sizes;
    a guide formed in the interior first side and the interior second side, the guide configured to slidably receive the modular containers and allow for slidable motion of the modular containers to and from the interior rear but to prevent motion of the modular containers to and from the interior bottom and the interior top; and
    a container lock configured to selectively permit and prevent the slidable motion of at least one of the modular containers to and from the interior rear;
    wherein the processor is operatively associated with the container lock;
    wherein the processor is configured to operate the container lock based on:
        the robotic unit being within a designated site in accordance with a delivery schedule; and
        the robotic unit receiving validation information in the form of an access code or a token that an individual is an authorized individual.

2. The system recited in claim 1, wherein the processor is configured to open the container lock when within the designated site.

3. The system recited in claim 1, wherein the processor is configured to open the container lock when it receives the validation information.

4. The system recited in claim 1, wherein the container lock comprises a lever arrangement and/or a magnet arrangement.

5. The system recited in claim 4, wherein:
    the lever arrangement comprises a electromechanically actuated plunger style lever having a catch, wherein the plunger is actuated by a motor that causes the catch to engage and disengage with a notch formed in the guide and a notch formed in the container; and
    the magnet arrangement comprises first magnetic element disposed on the housing and a second magnetic element disposed on the container, wherein the first magnetic element is a magnet or a material attractable by magnetic force, and the second magnetic element is a magnet or a material attractable by magnetic force, wherein when the first magnet element co-registers with the second magnetic element, the system identifies the type and placement of the container.

6. The system recited in claim 1, further comprising the container, the container having a container rail about a periphery of the container and configured to slidingly engage with the guide.

7. The system recited in claim 6, further comprising a locker-door hingedly attached to the container, the locker-door having a guide tab configured to slidingly engage the guide.

8. The system recited in claim 7, wherein the guide tab is configured to prevent rotation of the locker-door about the hinge when the guide tab is slidingly engaged with the guide.

9. The system recited in claim 8, wherein:
    the storage space is configured to allow:
        the container to slide along the guide towards the interior rear to a stowed position, the stowed position being defined as the guide tab being slidingly engaged with the guide so as to prevent rotation of the locker-door; and
        the container to slide along the guide away from the interior rear to an un-stowed position, the un-stowed position being defined as the guide tab being slidingly disengaged with the guide so as to allow rotation of the locker-door; and the container lock is configured to selectively lock the container in the stowed position.

10. The system recited in claim 6, wherein the container is configured to hold the items.

11. The system recited in claim 10, further comprising a plurality of containers, wherein:

the processor is configured to designate at least one container as a free container to be freely accessed by any individual having access to the robotic unit; and the processor is configured to designate at least one container as a restricted container to be accessed by the authorized individual for whom the items being delivered are designated.

12. The system recited in claim 1, wherein the robotic unit is configured to deviate from the determined or pre-determined route to achieve any one or combination of avoiding collisions, following a detour, and pursuing a more or less optimal path.

13. The system recited in claim 1, wherein:

the storage space is configured to allow:
the container to slide along the guide towards the interior rear to a stowed position; and
the container to slide along the guide away from the interior rear to an un-stowed position; and the container lock is configured to selectively lock the container in the stowed position.

14. The system recited in claim 1, further comprising a housing door configured to grant access to the storage space.

15. The system recited in claim 14, wherein the housing door is configured to grant selective access to the storage space based on:

the robotic unit being within a designated site in accordance with a delivery schedule; and the robotic unit receiving validation information in the form of an access code or a token that an individual is an authorized individual.

16. A method for delivery and chain of custody for items, the method comprising:

placing a first item in a first container and placing a second item in a second container;

designating the first item for delivery to a first individual and designating the second item for delivery to a second individual;

placing the first container and the second container in a storage space of a robotic unit;

locking the first container within the storage space and registering the first container as a restricted container only to be accessed by the first individual, and locking the second container within the storage space and registering the second container as a restricted container only to be accessed by the second individual;

causing the robotic unit to follow a predetermined path to deliver the first item to the first individual and the second item to the second individual in accordance with a delivery schedule, wherein while following the delivery schedule the robotic unit:

unlocks the first container only upon receiving validation information in the form of an access code or a token about the first individual; and unlocks the second container only upon receiving validation information in the form of an access code or a token about the second individual.

17. The method recited in claim 16, wherein the first and second containers are modular containers, and wherein the storage space is configured to receive a plurality of modular containers of different sizes.

18. The method recited in claim 17, further comprising:

placing a third item in a third modular container;

placing the third modular container in the storage space of the robotic unit;

registering the third modular container as a free container to be accessed by any individual, wherein while following the delivery schedule the robotic unit allows access to the third modular container by any individual only when the robotic unit is within a designated site in accordance with the delivery schedule.

19. A method for delivery and chain of custody for items, the method comprising:

placing a first item in a first container and placing a second item in a second container;

designating the first item for delivery to a first individual;

placing the first container and the second container in a storage space of the robotic unit;

locking the first container within the storage space and registering the first container as a restricted container only to be accessed by the first individual, and registering the second container as a free container to be accessed by any individual;

causing the robotic unit to follow a predetermined path to deliver the first item to the first individual in accordance with a delivery schedule, wherein while following the delivery schedule the robotic unit:

allows access to the second container by any individual only when the robotic unit is within a designated site in accordance with the delivery schedule;

unlocks the first container only upon receiving validation information in the form of an access code or a token about the first individual.

20. The method recited in claim 19, wherein the first and second containers are modular containers, and wherein the storage space is configured to receive a plurality of modular containers of different sizes.

* * * * *